US006274789B1

(12) United States Patent
Yano et al.

(10) Patent No.: US 6,274,789 B1
(45) Date of Patent: Aug. 14, 2001

(54) RICE GENE RESISTANT TO BLAST DISEASE

(75) Inventors: Masahiro Yano; Masao Iwamoto; Yuichi Katayose; Takuji Sasaki; Zi-Xuan Wang; Utako Yamanouchi; Lisa Ishimaru, all of Ibaraki (JP)

(73) Assignee: Society for Techno-Innovation of Agriculture, Forestry and Fisheries (JP)

( * ) Notice: Subject to any disclaimer, the term of this patent is extended or adjusted under 35 U.S.C. 154(b) by 0 days.

(21) Appl. No.: 09/330,330

(22) Filed: Jun. 11, 1999

(30) Foreign Application Priority Data

Jun. 12, 1998 (JP) .................................................. 10-181455

(51) Int. Cl.$^7$ ............................. C12N 5/04; C12N 15/09; C12N 15/29; C12N 15/82; A01H 5/00
(52) U.S. Cl. ......................... 800/279; 800/278; 800/295; 800/298; 800/320.2; 435/69.1; 435/320.1; 435/419; 435/468; 435/430; 536/23.1; 536/23.6
(58) Field of Search .................................... 800/279, 298, 800/295, 320.2, 278; 435/69.1, 320.1, 419, 468, 430; 536/23.1, 23.6

(56) References Cited

U.S. PATENT DOCUMENTS 5,674,993  10/1997  Kawasaki et al. .................. 536/23.6
5,675,929 * 10/1997  Sontea et al. ............................ 47/18

OTHER PUBLICATIONS

Iwata N., Rice Genetics Newsletter, vol. 13, pp. 12–35, 1996.
Kinoshita T., Rice Genetics Newsletter, vol. 7, pp. 16–57, 1990.
Iwata N., Rice Genetics Newsletter, vol. 14, pp. 9–22, 1997.
Wilfried Kramer and Hans–Joachim Fritz. "Methods in Enzymology", vol. 154, pp. 350–367, 1987.
E.M. Southern., J. Mol. Biol., vol. 98, pp. 503–517, 1975.
Randall K. Saiki., Science, vol. 230, pp. 1350–1354, 1985
Randall K. Saiki., Science, vol. 239, pp. 487–491, 1988.
Samuel Karlin and Stephen F. Altshul., Proc. Natl. Acad. Sci. USA., vol. 87, pp. 2264–2268, 1990.
Samuel Karlin and Stephen F. Altschul., Proc. Natl. Acad. Sci. USA, vol. 90, pp. 5873–5877, 1993.
Stephen F. Altschul. et al., J. Mol. Biol., vol. 215, pp. 403–410, 1990.
Stephen F. Altschul. et al. Nucleic Acids Research, vol. 25, No. 17, pp. 3389–3402, 1997.
M. Mandel and Higa A., J. Mol. Biol., vol. 53, pp. 159–162, 1970.
D. Hanahan. J. Mol. Biol., vol. 166, pp. 557–580, 1983.
Toki. S. et al., Plant Physiol., vol. 100, pp. 1503–1507, 1992.
Frederick M. Ausubel. et al., Current protocols in Molecular Biology., 6.3.1–6.3.5, 1993.
Hayasaka H. et al., Japanese Society of Breeding, the 87th meeting., p. 92, 1995.
Iwamoto m. et al., Japanese Society of Breeding, the 89th meeting., p. 227, 1986.
Gary A. Churchill. et al., Proc. National. Acad. Sci. USA., vol. 90, pp. 16–20, 1993.
Monna L. et al., Theor Appl Genet., vol. 94, pp. 170–176, 1997.
Geoffrey M. Wahl. et al., Proc. National Acad. Sci. USA., vol. 84, pp. 2160–2164, 1987.
Yoshimura et al. Proc. Natl. Acad. Sci. USA. vol. 95, pp. 1663–1668, Feb. 1998.*
Song et al. Science, vol. 270, pp. 1804–1806, Dec. 1995.*
Tu et al. Theor. Appl. Genet. vol. 97, pp. 31–36, Jan. 1998.*
Linthorst et al. The plant cell, vol. 1, pp. 285–291, Mar. 1989.*
Bennetzen et al. Genet. Eng. vol. 14, pp. 99–124, 1992.*

* cited by examiner

*Primary Examiner*—David T. Fox
*Assistant Examiner*—Medina A. Ibrahim
(74) *Attorney, Agent, or Firm*—Fish & Richardson P.C.

(57) ABSTRACT

A blast disease-resistance gene (Pi-b), a functionally equivalent gene thereof and proteins encoded by the genes are provided. The gene is useful for creating a plant resistant to the blast disease and can confer a resistance to a broad range of the rice blast fungi on plants. Therefore, it is useful for controlling the disease and increasing crop yields.

16 Claims, 4 Drawing Sheets

Fig. 4

| | P-loop | Kinase 2 | Domain 1 | Domain 2 | Domain 3 |
|---|---|---|---|---|---|
| RPM1 | GMGGSGKTTL | KRYIVVLDDVW | GSRVMMTTRDM | QGLPLAIASLGS | KRCFLYCS |
| RPS2 | GPGGVGKTTL | KRFLLLLDDVW | KCKVMFTTRSI | GGLPLALITLGG | RSCFLYCA |
| N | GMGGVGKTTI | KKVLIVLDDID | GSRIIITTRDK | KGLPLALKVWGS | IACFLRGE |
| L6 | GMGGIGKTTT | FKILVVLDDVD | QSRFIITSRSM | AGLPLTLKVIGS | IACFFIGQ |
| Xa1 | GNGGIGKTTL | KKFLIVLDDVW | GNMIILTTRIQ | KGNPLAAKTVGS | DQCVSYCS |
| c23 | GMGGLGKTTL | KSCLIVLDDFS | TSRIIVTTRKE | DGLPLAIVVIGG | KSCFLYLS |

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 1205 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:1:

```
Met Met Arg Ser Phe Met Met Glu Ala His Glu Gln Asp Asn Ser
 1               5                  10                  15

Lys Val Val Lys Thr Trp Val Lys Gln Val Arg Asp Thr Ala Tyr Asp
                20                  25                  30

Val Glu Asp Ser Leu Gln Asp Phe Ala Val His Leu Lys Arg Pro Ser
            35                  40                  45

Trp Trp Arg Phe Pro Arg Thr Leu Leu Glu Arg His Arg Val Ala Lys
 50                  55                  60

Gln Met Lys Glu Leu Arg Asn Lys Val Glu Asp Val Ser Gln Arg Asn
 65                  70                  75                  80

Val Arg Tyr His Leu Ile Lys Gly Ser Ala Lys Ala Thr Ile Asn Ser
                85                  90                  95

Thr Glu Gln Ser Ser Val Ile Ala Thr Ala Ile Phe Gly Ile Asp Asp
                100                 105                 110

Ala Arg Arg Ala Ala Lys Gln Asp Asn Gln Arg Val Asp Leu Val Gln
            115                 120                 125

Leu Ile Asn Ser Glu Asp Gln Asp Leu Lys Val Ile Ala Val Trp Gly
130                 135                 140

Thr Ser Gly Asp Met Gly Gln Thr Thr Ile Ile Arg Met Ala Tyr Glu
145                 150                 155                 160

Asn Pro Asp Val Gln Ile Arg Phe Pro Cys Arg Ala Trp Val Arg Val
                165                 170                 175

Met His Pro Phe Ser Pro Arg Asp Phe Val Gln Ser Leu Val Asn Gln
            180                 185                 190

Leu His Ala Thr Gln Gly Val Glu Ala Leu Leu Glu Lys Glu Lys Thr
            195                 200                 205

Glu Gln Asp Leu Ala Lys Lys Phe Asn Gly Cys Val Asn Asp Arg Lys
            210                 215                 220

Cys Leu Ile Val Leu Asn Asp Leu Ser Thr Ile Glu Glu Trp Asp Gln
225                 230                 235                 240

Ile Lys Lys Cys Phe Gln Lys Cys Arg Lys Gly Ser Arg Ile Ile Val
                245                 250                 255

Ser Ser Thr Gln Val Glu Val Ala Ser Leu Cys Ala Gly Gln Glu Ser
            260                 265                 270

Gln Ala Ser Glu Leu Lys Gln Leu Ser Ala Asp Gln Thr Leu Tyr Ala
            275                 280                 285

Phe Tyr Asp Lys Gly Ser Gln Ile Ile Glu Asp Ser Val Lys Pro Val
            290                 295                 300

Ser Ile Ser Asp Val Ala Ile Thr Ser Thr Asn Asn His Thr Val Ala
305                 310                 315                 320

His Gly Glu Ile Ile Asp Asp Gly Ser Met Asp Ala Asp Glu Lys Lys
                325                 330                 335

Val Ala Arg Lys Ser Leu Thr Arg Ile Arg Thr Ser Val Gly Ala Ser
            340                 345                 350

Glu Glu Ser Gln Leu Ile Gly Arg Glu Lys Glu Ile Ser Glu Ile Thr
            355                 360                 365

His Leu Ile Leu Asn Asn Asp Ser Gln Gln Val Gln Val Ile Ser Val
            370                 375                 380
```

-continued

```
Trp Gly Met Gly Gly Leu Gly Lys Thr Thr Leu Val Ser Gly Val Tyr
385                 390                 395                 400

Gln Ser Pro Arg Leu Ser Asp Lys Phe Asp Lys Tyr Val Phe Val Thr
            405                 410                 415

Ile Met Arg Pro Phe Ile Leu Val Glu Leu Leu Arg Ser Leu Ala Glu
            420                 425                 430

Gln Leu His Lys Gly Ser Ser Lys Lys Glu Glu Leu Leu Glu Asn Arg
            435                 440                 445

Val Ser Ser Lys Lys Ser Leu Ala Ser Met Glu Asp Thr Glu Leu Thr
        450                 455                 460

Gly Gln Leu Lys Arg Leu Leu Glu Lys Lys Ser Cys Leu Ile Val Leu
465                 470                 475                 480

Asp Asp Phe Ser Asp Thr Ser Glu Trp Asp Gln Ile Lys Pro Thr Leu
            485                 490                 495

Phe Pro Leu Leu Glu Lys Thr Ser Arg Ile Ile Val Thr Thr Arg Lys
            500                 505                 510

Glu Asn Ile Ala Asn His Cys Ser Gly Lys Asn Gly Asn Val His Asn
            515                 520                 525

Leu Lys Val Leu Lys His Asn Asp Ala Leu Cys Leu Leu Ser Glu Lys
        530                 535                 540

Val Phe Glu Glu Ala Thr Tyr Leu Asp Asp Gln Asn Asn Pro Glu Leu
545                 550                 555                 560

Val Lys Glu Ala Lys Gln Ile Leu Lys Lys Cys Asp Gly Leu Pro Leu
            565                 570                 575

Ala Ile Val Val Ile Gly Gly Phe Leu Ala Asn Arg Pro Lys Thr Pro
            580                 585                 590

Glu Glu Trp Arg Lys Leu Asn Glu Asn Ile Asn Ala Glu Leu Glu Met
            595                 600                 605

Asn Pro Glu Leu Gly Met Ile Arg Thr Val Leu Glu Lys Ser Tyr Asp
            610                 615                 620

Gly Leu Pro Tyr His Leu Lys Ser Cys Phe Leu Tyr Leu Ser Ile Phe
625                 630                 635                 640

Pro Glu Asp Gln Ile Ile Ser Arg Arg Arg Leu Val His Arg Trp Ala
            645                 650                 655

Ala Glu Gly Tyr Ser Thr Ala Ala His Gly Lys Ser Ala Ile Glu Ile
            660                 665                 670

Ala Asn Gly Tyr Phe Met Glu Leu Lys Asn Arg Ser Met Ile Leu Pro
            675                 680                 685

Phe Gln Gln Ser Gly Ser Ser Arg Lys Ser Ile Asp Ser Cys Lys Val
            690                 695                 700

His Asp Leu Met Arg Asp Ile Ala Ile Ser Lys Ser Thr Glu Glu Asn
705                 710                 715                 720

Leu Val Phe Arg Val Glu Glu Gly Cys Ser Ala Tyr Ile His Gly Ala
            725                 730                 735

Ile Arg His Leu Ala Ile Ser Ser Asn Trp Lys Gly Asp Lys Ser Glu
            740                 745                 750

Phe Glu Gly Ile Val Asp Leu Ser Arg Ile Arg Ser Leu Ser Leu Phe
            755                 760                 765

Gly Asp Trp Lys Pro Phe Phe Val Tyr Gly Lys Met Arg Phe Ile Arg
            770                 775                 780

Val Leu Asp Phe Glu Gly Thr Arg Gly Leu Glu Tyr His His Leu Asp
785                 790                 795                 800

Gln Ile Trp Lys Leu Asn His Leu Lys Phe Leu Ser Leu Arg Gly Cys
```

805                 810                 815
Tyr Arg Ile Asp Leu Leu Pro Asp Leu Leu Gly Asn Leu Arg Gln Leu
                820                 825                 830

Gln Met Leu Asp Ile Arg Gly Thr Tyr Val Lys Ala Leu Pro Lys Thr
            835                 840                 845

Ile Ile Lys Leu Gln Lys Leu Gln Tyr Ile His Ala Gly Arg Lys Thr
        850                 855                 860

Asp Tyr Val Trp Glu Glu Lys His Ser Leu Met Gln Arg Cys Arg Lys
865                 870                 875                 880

Val Gly Cys Ile Cys Ala Thr Cys Cys Leu Pro Leu Cys Glu Met
            885                 890                 895

Tyr Gly Pro Leu His Lys Ala Leu Ala Arg Arg Asp Ala Trp Thr Phe
            900                 905                 910

Ala Cys Cys Val Lys Phe Pro Ser Ile Met Thr Gly Val His Glu Glu
            915                 920                 925

Glu Gly Ala Met Val Pro Ser Gly Ile Arg Lys Leu Lys Asp Leu His
        930                 935                 940

Thr Leu Arg Asn Ile Asn Val Gly Arg Gly Asn Ala Ile Leu Arg Asp
945                 950                 955                 960

Ile Gly Met Leu Thr Gly Leu His Lys Leu Gly Val Ala Gly Ile Asn
            965                 970                 975

Lys Lys Asn Gly Arg Ala Phe Arg Leu Ala Ile Ser Asn Leu Asn Lys
            980                 985                 990

Leu Glu Ser Leu Ser Val Ser Ser Ala Gly Met Pro Gly Leu Cys Gly
        995                 1000                1005

Cys Leu Asp Asp Ile Ser Ser Pro Glu Asn Leu Gln Ser Leu Lys
        1010                1015                1020

Leu Tyr Gly Ser Leu Lys Thr Leu Pro Glu Trp Ile Lys Glu Leu Gln
1025                1030                1035                1040

His Leu Val Lys Leu Lys Leu Val Ser Thr Arg Leu Leu Glu His Asp
            1045                1050                1055

Val Ala Met Glu Phe Leu Gly Glu Leu Pro Lys Val Glu Ile Leu Val
            1060                1065                1070

Ile Ser Pro Phe Lys Ser Glu Glu Ile His Phe Lys Pro Pro Gln Thr
        1075                1080                1085

Gly Thr Ala Phe Val Ser Leu Arg Val Leu Lys Leu Ala Gly Leu Trp
        1090                1095                1100

Gly Ile Lys Ser Val Lys Phe Glu Glu Gly Thr Met Pro Lys Leu Glu
1105                1110                1115                1120

Arg Leu Gln Val Gln Gly Arg Ile Glu Asn Glu Ile Gly Phe Ser Gly
            1125                1130                1135

Leu Glu Phe Leu Gln Asn Ile Asn Glu Val Gln Leu Ser Val Trp Phe
            1140                1145                1150

Pro Thr Asp His Asp Arg Ile Arg Ala Ala Arg Ala Ala Gly Ala Asp
        1155                1160                1165

Tyr Glu Thr Ala Trp Glu Glu Val Gln Glu Ala Arg Arg Lys Gly
        1170                1175                1180

Gly Glu Leu Lys Arg Lys Ile Arg Glu Gln Leu Ala Arg Asn Pro Asn
1185                1190                1195                1200

Gln Pro Ile Ile Thr
        1205

(2) INFORMATION FOR SEQ ID NO:2:

(i) SEQUENCE CHARACTERISTICS:
    (A) LENGTH: 3925 base pairs
    (B) TYPE: nucleic acid
    (C) STRANDEDNESS: double
    (D) TOPOLOGY: linear (ii) MOLECULE TYPE: cDNA to mRNA (ix) FEATURE:
    (A) NAME/KEY: Coding Sequence
    (B) LOCATION: 82...3696

(xi) SEQUENCE DESCRIPTION: SEQ ID NO:2:

```
GCAAAATCTG CATTTGCTGA GGAGGTGGCC TTGCAGCTTG GTATCCAGAA AGACCACACA          60

TTTGTTGCAG ATGAGCTTGA G ATG ATG AGG TCT TTC ATG ATG GAG GCG CAC          111
                         Met Met Arg Ser Phe Met Met Glu Ala His
                          1               5                  10

GAG GAG CAA GAT AAC AGC AAG GTG GTC AAG ACT TGG GTG AAG CAA GTC          159
Glu Glu Gln Asp Asn Ser Lys Val Val Lys Thr Trp Val Lys Gln Val
                15                  20                  25

CGT GAC ACT GCC TAT GAT GTT GAG GAC AGC CTC CAG GAT TTC GCT GTT          207
Arg Asp Thr Ala Tyr Asp Val Glu Asp Ser Leu Gln Asp Phe Ala Val
            30                  35                  40

CAT CTT AAG AGG CCA TCC TGG TGG CGA TTT CCT CGT ACG CTG CTC GAG          255
His Leu Lys Arg Pro Ser Trp Trp Arg Phe Pro Arg Thr Leu Leu Glu
        45                  50                  55

CGG CAC CGT GTG GCC AAG CAG ATG AAG GAG CTT AGG AAC AAG GTC GAG          303
Arg His Arg Val Ala Lys Gln Met Lys Glu Leu Arg Asn Lys Val Glu
    60                  65                  70

GAT GTC AGC CAG AGG AAT GTG CGG TAC CAC CTC ATC AAG GGC TCT GCC          351
Asp Val Ser Gln Arg Asn Val Arg Tyr His Leu Ile Lys Gly Ser Ala
75                  80                  85                  90

AAG GCC ACC ATC AAT TCC ACT GAG CAA TCT AGC GTT ATT GCT ACA GCC          399
Lys Ala Thr Ile Asn Ser Thr Glu Gln Ser Ser Val Ile Ala Thr Ala
                95                  100                 105

ATA TTC GGC ATT GAC GAT GCA AGG CGT GCC GCA AAG CAG GAC AAT CAG          447
Ile Phe Gly Ile Asp Asp Ala Arg Arg Ala Ala Lys Gln Asp Asn Gln
            110                 115                 120

AGA GTG GAT CTT GTC CAA CTA ATC AAC AGT GAG GAT CAG GAC CTA AAA          495
Arg Val Asp Leu Val Gln Leu Ile Asn Ser Glu Asp Gln Asp Leu Lys
        125                 130                 135

GTG ATC GCG GTC TGG GGA ACA AGT GGT GAT ATG GGC CAA ACA ACA ATA          543
Val Ile Ala Val Trp Gly Thr Ser Gly Asp Met Gly Gln Thr Thr Ile
    140                 145                 150

ATC AGG ATG GCT TAT GAG AAC CCA GAT GTC CAA ATC AGA TTC CCA TGC          591
Ile Arg Met Ala Tyr Glu Asn Pro Asp Val Gln Ile Arg Phe Pro Cys
155                 160                 165                 170

CGT GCA TGG GTA AGG GTG ATG CAT CCT TTC AGT CCA AGA GAC TTT GTC          639
Arg Ala Trp Val Arg Val Met His Pro Phe Ser Pro Arg Asp Phe Val
                175                 180                 185

CAG AGC TTG GTG AAT CAG CTT CAT GCA ACC CAA GGG GTT GAA GCT CTG          687
Gln Ser Leu Val Asn Gln Leu His Ala Thr Gln Gly Val Glu Ala Leu
            190                 195                 200

TTG GAG AAA GAG AAG ACA GAA CAA GAT TTA GCT AAG AAA TTC AAT GGA          735
Leu Glu Lys Glu Lys Thr Glu Gln Asp Leu Ala Lys Lys Phe Asn Gly
        205                 210                 215

TGT GTG AAT GAT AGG AAG TGT CTA ATT GTG CTT AAT GAC CTA TCC ACC          783
Cys Val Asn Asp Arg Lys Cys Leu Ile Val Leu Asn Asp Leu Ser Thr
    220                 225                 230

ATT GAA GAG TGG GAC CAG ATT AAG AAA TGC TTC CAA AAA TGC AGG AAA          831
Ile Glu Glu Trp Asp Gln Ile Lys Lys Cys Phe Gln Lys Cys Arg Lys
```

```
                                                        -continued 235                   240                   245                         250

GGA AGC CGA ATC ATA GTG TCA AGC ACT CAA GTT GAA GTT GCA AGC TTA                879
Gly Ser Arg Ile Ile Val Ser Ser Thr Gln Val Glu Val Ala Ser Leu
                255                   260                   265

TGT GCT GGG CAA GAA AGC CAA GCC TCA GAG CTA AAG CAA TTG TCT GCT                927
Cys Ala Gly Gln Glu Ser Gln Ala Ser Glu Leu Lys Gln Leu Ser Ala
                270                   275                   280

GAT CAG ACC CTT TAC GCA TTC TAC GAC AAG GGT TCC CAA ATT ATA GAG                975
Asp Gln Thr Leu Tyr Ala Phe Tyr Asp Lys Gly Ser Gln Ile Ile Glu
                285                   290                   295

GAT TCA GTG AAG CCA GTG TCT ATC TCG GAT GTG GCC ATC ACA AGT ACA               1023
Asp Ser Val Lys Pro Val Ser Ile Ser Asp Val Ala Ile Thr Ser Thr
                300                   305                   310

AAC AAT CAT ACA GTG GCC CAT GGT GAG ATT ATA GAT GAT CAA TCA ATG               1071
Asn Asn His Thr Val Ala His Gly Glu Ile Ile Asp Asp Gln Ser Met
315                   320                   325                   330

GAT GCT GAT GAG AAG AAG GTG GCT AGA AAG AGT CTT ACT CGC ATT AGG               1119
Asp Ala Asp Glu Lys Lys Val Ala Arg Lys Ser Leu Thr Arg Ile Arg
                335                   340                   345

ACA AGT GTT GGT GCT TCG GAG GAA TCA CAA CTT ATT GGG CGA GAG AAA               1167
Thr Ser Val Gly Ala Ser Glu Glu Ser Gln Leu Ile Gly Arg Glu Lys
                350                   355                   360

GAA ATA TCT GAA ATA ACA CAC TTA ATT TTA AAC AAT GAT AGC CAG CAG               1215
Glu Ile Ser Glu Ile Thr His Leu Ile Leu Asn Asn Asp Ser Gln Gln
                365                   370                   375

GTT CAG GTG ATC TCT GTG TGG GGA ATG GGT GGC CTT GGA AAA ACC ACC               1263
Val Gln Val Ile Ser Val Trp Gly Met Gly Gly Leu Gly Lys Thr Thr
380                   385                   390

CTA GTA AGC GGT GTT TAT CAA AGC CCA AGG CTG AGT GAT AAG TTT GAC               1311
Leu Val Ser Gly Val Tyr Gln Ser Pro Arg Leu Ser Asp Lys Phe Asp
395                   400                   405                   410

AAG TAT GTT TTT GTC ACA ATC ATG CGT CCT TTC ATT CTT GTA GAG CTC               1359
Lys Tyr Val Phe Val Thr Ile Met Arg Pro Phe Ile Leu Val Glu Leu
                415                   420                   425

CTT AGG AGT TTG GCT GAG CAA CTA CAT AAA GGA TCT TCT AAG AAG GAA               1407
Leu Arg Ser Leu Ala Glu Gln Leu His Lys Gly Ser Ser Lys Lys Glu
                430                   435                   440

GAA CTG TTA GAA AAT AGA GTC AGC AGT AAG AAA TCA CTA GCA TCG ATG               1455
Glu Leu Leu Glu Asn Arg Val Ser Ser Lys Lys Ser Leu Ala Ser Met
                445                   450                   455

GAG GAT ACC GAG TTG ACT GGG CAG TTG AAA AGG CTT TTA GAA AAG AAA               1503
Glu Asp Thr Glu Leu Thr Gly Gln Leu Lys Arg Leu Leu Glu Lys Lys
                460                   465                   470

AGT TGC TTG ATT GTT CTA GAT GAT TTC TCA GAT ACC TCA GAA TGG GAC               1551
Ser Cys Leu Ile Val Leu Asp Asp Phe Ser Asp Thr Ser Glu Trp Asp
475                   480                   485                   490

CAG ATA AAA CCA ACG TTA TTC CCC CTG TTG GAA AAG ACA AGC CGA ATA               1599
Gln Ile Lys Pro Thr Leu Phe Pro Leu Leu Glu Lys Thr Ser Arg Ile
                495                   500                   505

ATT GTG ACT ACA AGA AAA GAG AAT ATT GCC AAC CAT TGC TCA GGG AAA               1647
Ile Val Thr Thr Arg Lys Glu Asn Ile Ala Asn His Cys Ser Gly Lys
                510                   515                   520

AAT GGA AAT GTG CAC AAC CTT AAA GTT CTT AAA CAT AAT GAT GCA TTG               1695
Asn Gly Asn Val His Asn Leu Lys Val Leu Lys His Asn Asp Ala Leu
                525                   530                   535

TGC CTC TTG AGT GAG AAG GTA TTT GAG GAG GCT ACA TAT TTG GAT GAT               1743
Cys Leu Leu Ser Glu Lys Val Phe Glu Glu Ala Thr Tyr Leu Asp Asp
                540                   545                   550

CAG AAC AAT CCA GAG TTG GTT AAA GAA GCA AAA CAA ATC CTA AAG AAG               1791
```

```
Gln Asn Asn Pro Glu Leu Val Lys Glu Ala Lys Gln Ile Leu Lys Lys
555                 560                 565                 570

TGC GAT GGA CTG CCC CTT GCA ATA GTT GTC ATA GGT GGA TTC TTG GCA    1839
Cys Asp Gly Leu Pro Leu Ala Ile Val Val Ile Gly Gly Phe Leu Ala
                575                 580                 585

AAC CGA CCA AAG ACC CCA GAA GAG TGG AGA AAA TTG AAC GAG AAT ATC    1887
Asn Arg Pro Lys Thr Pro Glu Glu Trp Arg Lys Leu Asn Glu Asn Ile
                590                 595                 600

AAT GCT GAG TTG GAA ATG AAT CCA GAG CTT GGA ATG ATA AGA ACC GTC    1935
Asn Ala Glu Leu Glu Met Asn Pro Glu Leu Gly Met Ile Arg Thr Val
            605                 610                 615

CTT GAA AAA AGC TAT GAT GGT TTA CCA TAC CAT CTC AAG TCA TGT TTT    1983
Leu Glu Lys Ser Tyr Asp Gly Leu Pro Tyr His Leu Lys Ser Cys Phe
620                 625                 630

TTA TAT CTG TCC ATT TTC CCT GAA GAC CAG ATC ATT AGT CGA AGG CGT    2031
Leu Tyr Leu Ser Ile Phe Pro Glu Asp Gln Ile Ile Ser Arg Arg Arg
635                 640                 645                 650

TTG GTG CAT CGT TGG GCA GCA GAA GGT TAC TCA ACT GCA GCA CAT GGG    2079
Leu Val His Arg Trp Ala Ala Glu Gly Tyr Ser Thr Ala Ala His Gly
                655                 660                 665

AAA TCT GCC ATT GAA ATA GCT AAC GGC TAC TTC ATG GAA CTC AAG AAT    2127
Lys Ser Ala Ile Glu Ile Ala Asn Gly Tyr Phe Met Glu Leu Lys Asn
                670                 675                 680

AGA AGC ATG ATT TTA CCA TTC CAG CAA TCA GGT AGC AGC AGG AAA TCA    2175
Arg Ser Met Ile Leu Pro Phe Gln Gln Ser Gly Ser Ser Arg Lys Ser
            685                 690                 695

ATT GAC TCT TGC AAA GTC CAT GAT CTC ATG CGT GAC ATC GCC ATC TCA    2223
Ile Asp Ser Cys Lys Val His Asp Leu Met Arg Asp Ile Ala Ile Ser
            700                 705                 710

AAG TCA ACG GAG GAA AAC CTT GTT TTT AGG GTG GAG GAA GGC TGC AGC    2271
Lys Ser Thr Glu Glu Asn Leu Val Phe Arg Val Glu Glu Gly Cys Ser
715                 720                 725                 730

GCG TAC ATA CAT GGT GCA ATT CGT CAT CTT GCT ATA AGT AGC AAC TGG    2319
Ala Tyr Ile His Gly Ala Ile Arg His Leu Ala Ile Ser Ser Asn Trp
                735                 740                 745

AAG GGA GAT AAG AGT GAA TTC GAG GGC ATA GTG GAC CTG TCC CGA ATA    2367
Lys Gly Asp Lys Ser Glu Phe Glu Gly Ile Val Asp Leu Ser Arg Ile
                750                 755                 760

CGA TCG TTA TCT CTG TTT GGG GAT TGG AAG CCA TTT TTT GTT TAT GGC    2415
Arg Ser Leu Ser Leu Phe Gly Asp Trp Lys Pro Phe Phe Val Tyr Gly
            765                 770                 775

AAG ATG AGG TTT ATA CGA GTG CTT GAC TTT GAA GGG ACT AGA GGT CTA    2463
Lys Met Arg Phe Ile Arg Val Leu Asp Phe Glu Gly Thr Arg Gly Leu
780                 785                 790

GAA TAT CAT CAC CTT GAT CAG ATT TGG AAG CTT AAT CAC CTA AAA TTC    2511
Glu Tyr His His Leu Asp Gln Ile Trp Lys Leu Asn His Leu Lys Phe
795                 800                 805                 810

CTT TCT CTA CGA GGA TGC TAT CGT ATT GAT CTA CTG CCA GAT TTA CTG    2559
Leu Ser Leu Arg Gly Cys Tyr Arg Ile Asp Leu Leu Pro Asp Leu Leu
                815                 820                 825

GGC AAC CTG AGG CAA CTC CAG ATG CTA GAC ATC AGA GGT ACA TAT GTA    2607
Gly Asn Leu Arg Gln Leu Gln Met Leu Asp Ile Arg Gly Thr Tyr Val
            830                 835                 840

AAG GCT TTG CCA AAA ACC ATC ATC AAG CTT CAG AAG CTA CAG TAC ATT    2655
Lys Ala Leu Pro Lys Thr Ile Ile Lys Leu Gln Lys Leu Gln Tyr Ile
            845                 850                 855

CAT GCT GGG CGC AAA ACA GAC TAT GTA TGG GAG GAA AAG CAT AGT TTA    2703
His Ala Gly Arg Lys Thr Asp Tyr Val Trp Glu Glu Lys His Ser Leu
        860                 865                 870
```

```
ATG CAG AGG TGT CGT AAG GTG GGA TGT ATA TGT GCA ACA TGT TGC CTC      2751
Met Gln Arg Cys Arg Lys Val Gly Cys Ile Cys Ala Thr Cys Cys Leu
875             880                 885                 890

CCT CTT CTT TGC GAA ATG TAT GGC CCT CTC CAT AAG GCC CTA GCC CGG      2799
Pro Leu Leu Cys Glu Met Tyr Gly Pro Leu His Lys Ala Leu Ala Arg
            895                 900                 905

CGT GAT GCG TGG ACT TTC GCT TGC TGC GTG AAA TTC CCA TCT ATC ATG      2847
Arg Asp Ala Trp Thr Phe Ala Cys Cys Val Lys Phe Pro Ser Ile Met
        910                 915                 920

ACG GGA GTA CAT GAA GAG GAA GGC GCT ATG GTG CCA AGT GGG ATT AGA      2895
Thr Gly Val His Glu Glu Glu Gly Ala Met Val Pro Ser Gly Ile Arg
                925                 930                 935

AAA CTG AAA GAC TTG CAC ACA CTA AGG AAC ATA AAT GTC GGA AGG GGA      2943
Lys Leu Lys Asp Leu His Thr Leu Arg Asn Ile Asn Val Gly Arg Gly
    940                 945                 950

AAT GCC ATC CTA CGA GAT ATC GGA ATG CTC ACA GGA TTA CAC AAG TTA      2991
Asn Ala Ile Leu Arg Asp Ile Gly Met Leu Thr Gly Leu His Lys Leu
955                 960                 965                 970

GGA GTG GCT GGC ATC AAC AAG AAG AAT GGA CGA GCG TTT CGC TTG GCC      3039
Gly Val Ala Gly Ile Asn Lys Lys Asn Gly Arg Ala Phe Arg Leu Ala
                975                 980                 985

ATT TCC AAC CTC AAC AAG CTG GAA TCA CTG TCT GTG AGT TCA GCA GGG      3087
Ile Ser Asn Leu Asn Lys Leu Glu Ser Leu Ser Val Ser Ser Ala Gly
            990                 995                 1000

ATG CCG GGC TTG TGT GGT TGC TTG GAT GAT ATA TCC TCG CCT CCG GAA      3135
Met Pro Gly Leu Cys Gly Cys Leu Asp Asp Ile Ser Ser Pro Pro Glu
        1005                1010                1015

AAC CTA CAG AGC CTC AAG CTG TAC GGC AGT TTG AAA ACG TTG CCG GAA      3183
Asn Leu Gln Ser Leu Lys Leu Tyr Gly Ser Leu Lys Thr Leu Pro Glu
    1020                1025                1030

TGG ATC AAG GAG CTC CAG CAT CTC GTG AAG TTA AAA CTA GTG AGT ACT      3231
Trp Ile Lys Glu Leu Gln His Leu Val Lys Leu Lys Leu Val Ser Thr
1035                1040                1045                1050

AGG CTA TTG GAG CAC GAC GTT GCT ATG GAA TTC CTT GGG GAA CTA CCG      3279
Arg Leu Leu Glu His Asp Val Ala Met Glu Phe Leu Gly Glu Leu Pro
                1055                1060                1065

AAG GTG GAA ATT CTA GTT ATT TCA CCG TTT AAG AGT GAA GAA ATT CAT      3327
Lys Val Glu Ile Leu Val Ile Ser Pro Phe Lys Ser Glu Glu Ile His
            1070                1075                1080

TTC AAG CCT CCG CAG ACT GGG ACT GCT TTT GTA AGC CTC AGG GTG CTC      3375
Phe Lys Pro Pro Gln Thr Gly Thr Ala Phe Val Ser Leu Arg Val Leu
        1085                1090                1095

AAG CTT GCA GGA TTA TGG GGC ATC AAA TCA GTG AAG TTT GAG GAA GGA      3423
Lys Leu Ala Gly Leu Trp Gly Ile Lys Ser Val Lys Phe Glu Glu Gly
    1100                1105                1110

ACA ATG CCC AAA CTT GAG AGG CTG CAG GTC CAA GGG CGA ATA GAA AAT      3471
Thr Met Pro Lys Leu Glu Arg Leu Gln Val Gln Gly Arg Ile Glu Asn
1115                1120                1125                1130

GAA ATT GGC TTT TCT GGG TTA GAG TTT CTC CAA AAC ATC AAC GAA GTC      3519
Glu Ile Gly Phe Ser Gly Leu Glu Phe Leu Gln Asn Ile Asn Glu Val
                1135                1140                1145

CAG CTC AGT GTT TGG TTT CCC ACG GAT CAT GAT AGG ATA AGA GCC GCG      3567
Gln Leu Ser Val Trp Phe Pro Thr Asp His Asp Arg Ile Arg Ala Ala
            1150                1155                1160

CGC GCC GCG GGC GCT GAT TAT GAG ACT GCC TGG GAG GAA GAG GTA CAG      3615
Arg Ala Ala Gly Ala Asp Tyr Glu Thr Ala Trp Glu Glu Glu Val Gln
        1165                1170                1175

GAA GCA AGG CGC AAG GGA GGT GAA CTG AAG AGG AAA ATC CGA GAA CAG      3663
Glu Ala Arg Arg Lys Gly Gly Glu Leu Lys Arg Lys Ile Arg Glu Gln
    1180                1185                1190
```

| | | | | | | | |
|---|---|---|---|---|---|---|---|
| CTT | GCT | CGG | AAT | CCA | AAC | CAA | CCC | ATC | ATT | ACC | TGAGCTCCTT | TGGAGTTACT | 3716 |
| Leu | Ala | Arg | Asn | Pro | Asn | Gln | Pro | Ile | Ile | Thr | | |
| 1195 | | | | 1200 | | | | | 1205 | | | |

TTGCCGTGCT CCATACTATC CTACAAGTGA GATCCTCTGC AGTACTGCAT GCTCACTGAC    3776

ATGTGGACCC GAGGGGCTGT GGGGCCCACA TGTCAGTGAG CAGTACTGTG CAGTACTGCA    3836

GAGGACCTGC ATCCACTATC CTATATTATA ATGGATTGTA CTATCGATCC AACTATTCAG    3896

ATTAACTCTA TACTAGTGAA CTTATTTTT    3925

(2) INFORMATION FOR SEQ ID NO:3:

(i) SEQUENCE CHARACTERISTICS:
        (A) LENGTH: 10322 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

CGGCCGCATA ATACGACTCA CTATAGGGAT CTCCTCTAGA GTTACTTTGC CGTGCTCCAT      60

ACTATCCTAT TCTATATTGG ATTATACTAT CGATCCAACG ATTCAGATTA ACTCTATACT     120

AGTGAAGTCT ACACTTATGG TATGGGTAAT ATACATATGT AGTATAGTAT AGCATAAGGG     180

TATTTCATTT TGCAGGTTAG CCGTTTATCT GCTGGTGCTC CTCTTGCTGT AGTAGTGTTG     240

TTGGTGTTGC TGCTGATGAC CTAAAATGCT TGCATGTTTC TATCATGTTC TCCATAATGT     300

AGTATCATGT ACTCCATCTT CCTTGTTGGT TTTTGTCCAT AATCTCCACC TTGGCAGCTT     360

GCATCATCTT ACTCTCGAGC TTGTCCACCT TGAGATTCAA CTCCTGGAAC GCGGCTCCCA     420

GTTCATCCAC CCTCTTCTCC ACGGCAGGAA TCCGTGACTC CACCGTACGC TTGAGATCTT     480

GGTACTCCGC CCTGGTGCGC TCATCAGCCT CAACTCGTTT CTTCTCATTC CCTTCCACAA     540

GTTGCAGAAG GAGGTCCAAC TTCTTATCAG TCTCCATGGC CTCGGATCTG GATCAGGTAC     600

CTACTGCTCT CGCTCCGAAT TCCGCGAACC TTAGGGGGCA AGTTTCCTTT TCGCGGTGCC     660

GATCCGAAGA TCAGCTCCAA TCCACCCCAA GGAACAATTT CACCGCAGAA TCAAGAGAAT     720

TTGAAGCA AGAGAGGCTC TGATACCAGA TTGTCAGGAT CTCAAGAAAT CAGCAAAGAA     780

CAACAAGAAC ACACAAGGAT TCAGGCAACT AGTTTGGATT GATCTGCTCC AACCCAACAG     840

GATTGAGCCT TCCGCCGCCA CCGCCACCGA GTTGCCAGTT CATAGTTGTC TTTCTCGAGT     900

TCATCTTATT TATACAGTAG TATCTCCCTA CTCACACGAC ACACACAGTA GCCAGCTGTA     960

CAACAGATAG CTGGGCTACG CAACCCACTC GGACCCATGG TAACGAGGAT TGGGCTTTGG    1020

CCCTCTTGTG GGTCTTGCTC TTCCTGGAGT AGTAGTCTGT ATCTCCTCCT CCTGGACTTC    1080

AGCTTCTGCT TCATCAGGTT CTCCTTCTTC AGGTTCCTTC TCTCCCTGTT CAGCTTCTGC    1140

TTCATCAGGT TCTCCTTCTT CAGTACCCAT AGTGACAGGC AGGTTCCTGA CAAAATTCTG    1200

CTCGTTTGCG ACCAATGGTA GTGATCATAG TTGCAACCAG GAGGGGGGG GGGGAAATCG    1260

CCGTCCCCTC CGCTCCTCTC CCGTCGTCCC CAACGCCTCG TTCGCGCATT TCGTTGAACA    1320

CCATGACGGC GCCGAATTCG CAGTGTCCGC ACATCTCCTC CTCCCCCGTC CTCTCCAAAC    1380

CCCAAACCCT ATCTCCACCC CCGAGGCAGG CGCCCCCATG CACTTGTAAG TCGATTGGAT    1440

GTCCTGTCCC AGAAGACATA TCGAGCGAGG AGGCGGAGGG GGACGAAGGG AACATATCGA    1500

GCGAGGAAGC GGAGGGTGGA TCGGCATCCC CCATTTCAAG GTACTATACT AGTCCATTAT    1560

AGTAGTAGTG CTTTTGCATC TTAGAAAAAA AAATATGTTC ATTAGCCATT GAGAGCTTCT    1620

```
GAAGTTGTTG ATTTTGTTCC AACCCCAACT GTGAGTTTCA GTTCAGGTCA TCCACTGATT    1680

TTCACTATGC CAATTCTCTG AAACAACTTT ACCACTGTCA CATGAACACA CTGAAACAGT    1740

TTGGTGTAGA CGTGTAGTGA AGAATGTAGC ATATATACCT TCACTTAATT TTTCTTGCAA    1800

TTATTGGCCA TTACTAGTTA TGCGAGGTAG AAGTGTTCTA AGGTACTGTA TCATTTTTAT    1860

GTACTAATTA ATTAAGTTTA ATAAAAACTT TTATTATCTA AAAATAAATG ACTATTACTA    1920

GCTCGGTACT CCCTTTATTT TATATTATAA GACGTTTTGA TTTTTTTATA TACAACTTTC    1980

TTTAAGTTTG ATTATACTTA TAAAAAATTA GCAAACATAT ATATTTTTTT TACATTAATA    2040

GTGCAAGTGA GCACGCTTAA ATGCATTGTA CTTCCTTCGT AAAAAAACAT CAAACTTTTA    2100

CGGACGAATA TGGATAAATG CATATCTAAA TTCATCCTCA ATAATTGATT CTTTTTGGAG    2160

GAGTACAATT GGTTGGTGCG CTTTGTCCTT GGACCCTACA ATAATGATGA TTGTTTCTTT    2220

AATCTATTGA CCTTGACTTA CCACATGGGC TATGTTTATC CCTTCCTGAA TCCTGAGCAC    2280

TGACTACCGA GGCACCGAGT GTGAGCGGCA ACGGCGGTCA GGGAGCAGGC GTGGCTCGTC    2340

GGCGAGCGGC TACGGGCAAC GGCGCCTTGG CGTCAGGCAT CCGCCGTCAC TCACCTCAAG    2400

CTTGCGGGCT CTGCGACCAC CCTCTCATAG TCATAGGCCA CAGAAGGTGT AGTAGTACTT    2460

CATACATTTC GAGCAGTTTC TTTCAGATTG TTTGTTTTTG AGCTTCTAAT TTTGGGATGC    2520

ATTAGATAGT GATGAAAGCC TGAATTATTG GAATTTTGGT GTTGGTACTC ACACTCTCAC    2580

AGTCAGAACA TACTCCTATA TATTTTGCAG CACATTTGCC TTGTGCGTGC TGTTCGTCTG    2640

TTCCACTCGT GAACATCAGA CGCGAAGATT ATAGATTCAC CCCTGTTCAC AGATTCAGGT    2700

ACTGCCAATT GCCTGGATGA ACACCAGTCC ATTTGCTCTC TTTCGCCTTA CAATTTTTCT    2760

CTGCATTGTA CTAGCAGCCG TAGCTCGAAA GCCTCGAATA TGATTCCTTT TCAAGATTTT    2820

ATATTTATGG AATATAATTC ACTTTTAAGA TGCCTTGATG GTGAAATAGT AGACATGTGA    2880

GACTCCAAAT CTCGTCCTAA AAGAGCATGG AGGTAAAAAA AGAAAAAGGT AGACATCGCT    2940

ATTGTAGACA TGGAGAGCTG GAATACGATT ACTTTCAAGA TATTATATTC AATGAGCATT    3000

CATTCTTACA CATATGCCAC AAAGGTAAAA AAAAACAGAG AAAGAGAGAG AGAGGGGAAA    3060

GAAGCCAAGT TCTTTCTTCT ACTATCATTT AGGTTGAGTT CGTTTGTTAA GGTTCCCAAC    3120

CTACGATTCC TCGTTTCCCG CGTGCACGAT TCCCAAACTA CTAAATGGTA TGCTTTTTAA    3180

AATATTTCGT AGAAAAATTG CTTTAAAAAA TCATATTAAT TTATTTTTTA AGTTGTTTAG    3240

CTAATACTCA ATTAATCATG CATTAATTTG CCGCTCCGTT TTAGTGGAAG TCATCTGAAA    3300

GGATCAAAGG AAGCAACACC AAGTCCTTAT TTCGACTCCG ACTCTCTCAC TCTCGCCATT    3360

TATTCTTTTC TTTCTGTTAT TTTAAAAGTT GCTACTTTAG CTTCAGCCAC GTGAATTCTT    3420

GATATTTCAT TATTTTTCTC ATCAAACAAT AGCATCTTCT TCTGGAAATC GAATTCAGGG    3480

CTTATATGTT GCTTATTCTG ATATATAGGT CTGTCACGAG GCGTATGATC ATCAACTCTG    3540

CCACAAAATC CATTCAAAAA TAGAACAGAG CAATGGAGGC GACGGCGCTG AGTGTGGGCA    3600

AATCCGTGCT GAATGGAGCG CTTGGCTACG CAAAATCTGC ATTTGCTGAG GAGGTGGCCT    3660

TGCAGCTTGG TATCCAGAAA GACCACACAT TTGTTGCAGA TGAGCTTGAG ATGATGAGGT    3720

CTTTCATGAT GGAGGCGCAC GAGGAGCAAG ATAACAGCAA GGTGGTCAAG ACTTGGGTGA    3780

AGCAAGTCCG TGACACTGCC TATGATGTTG AGGACAGCCT CCAGGATTTC GCTGTTCATC    3840

TTAAGAGGCC ATCCTGGTGG CGATTTCCTC GTACGCTGCT CGAGCGGCAC CGTGTGGCCA    3900

AGCAGATGAA GGAGCTTAGG AACAAGGTCG AGGATGTCAG CCAGAGGAAT GTGCGGTACC    3960
```

```
ACCTCATCAA GGGCTCTGCC AAGGCCACCA TCAATTCCAC TGAGCAATCT AGCGTTATTG   4020

CTACAGCCAT ATTCGGCATT GACGATGCAA GGCGTGCCGC AAAGCAGGAC AATCAGAGAG   4080

TGGATCTTGT CCAACTAATC AACAGTGAGG ATCAGGACCT AAAAGTGATC GCGGTCTGGG   4140

GAACAAGTGG TGATATGGGC CAAACAACAA TAATCAGGAT GGCTTATGAG AACCCAGATG   4200

TCCAAATCAG ATTCCCATGC CGTGCATGGG TAAGGGTGTG GCATCCTTTC AGTCCAAGAG   4260

ACTTTGTCCA GAGCTTGGTG AATCAGCTTC ATGCAACCCA AGGGGTTGAA GCTCTGTTGG   4320

AGAAAGAGAA GACAGAACAA GATTTAGCTA AGAAATTCAA TGGATGTGTG AATGATAGGA   4380

AGTGTCTAAT TGTGCTTAAT GACCTATCCA CCATTGAAGA GTGGGACCAG ATTAAGAAAT   4440

GCTTCCAAAA ATGCAGGAAA GGAAGCCGAA TCATAGTGTC AAGCACTCAA GTTGAAGTTG   4500

CAAGCTTATG TGCTGGGCAA GAAAGCCAAG CCTCAGAGCT AAAGCAATTG TCTGCTGATC   4560

AGACCCTTTA CGCATTCTAC GACAAGGTAA TATACTTGCT CTTCAAGCAT ACCTCTCGAT   4620

ATCATTTTTA ATTCAGTTAT GCCTTTAGTA ATTTCTAATT CAATTGTGTA TAGGCTAGTT   4680

GAAGTGCGTG GGAGTTACCA TTCCATTAGA AACACATGAC CTAATGCAAC TAACAAGTGC   4740

TCCTCCTGTT CTCTCTCATT TGCCTTTTGG GAATGCATGC ACTCAACATT TTAAGATTAC   4800

AGCCAAAATA TATGTATTTG GATTTGTCAA AACAAAGATG TATGCTAGAA AAAGAAATGG   4860

TCTAATACAG GTTTACAAAT AAGACAACGA TGCAAAAAGG GCAACTAAAA ACATATTGAT   4920

TCCCTCATCT GCCACTGCAA TTGCCTTAAA TTCTAGTCCA TTCTACTATC TCCGTTTCAT   4980

ATTATAAGTC ACTCTAGTTT TTTTCCAGTC AAACTTCTTT AGTTTGACCA AGTTTATACA   5040

AAAATTTAGC AACATATCCA ACACGAAATT AGTTTCATTA AATGTAGCAT TGAATATATT   5100

TTGATAGTAT GTTTGTTTTG TGTTGAAAAT GCTGCTATAT TTTTTAAAAA AACTTGGTCA   5160

AACCTAAACA AGTTTGACTA GGAGAAAAGT CGAAACGACT TATAATATGA AATAGAGGGA   5220

GAATGTTCGA AGTTTGGCTA ACGGTCAATG CTAGTGCTTT AAGTGGGTAA GCCGCAAATC   5280

CAATTATAGG CCAAAATACA TGGGTTTGTG GCTTATTTTG GCTATAAGTG GGTTTCGCGG   5340

GTTAGCCACT TACACCCCTA GTCAATGCTA ATGAAAGTAG AAGTGATGCT ATTCAAGGAA   5400

AATGTATTGG ATACCGAGAT TGCCTTGAAT AAAGAATAAA ATTGAGGTAG TAGATTGGAT   5460

AATAGATTGA CCCACAAAAT TGTACAAGTA TGTAATGTAG CACAAGTCCT CTTTGCACAA   5520

TTAAAATTTT GAAGCTCCTA TTTCACAAAT AATTTTGATA TGGATTAATT GATTTCATAT   5580

CCAATTCGCA CAGTTTATTG AATTTGGAGA TTTATTTCCT CTATATGTGA GAGATGATTG   5640

TAAAATGGGC AAATCTAGCA AATGCATCCT CTCATCCTTT GGATTAAATG TAGTGTACTT   5700

ATCCCATTAT TTTAAAGTTA AATTAATACA TATTTTATTG AACAGTCAGA TATACGTTTT   5760

TCAAAATAGG ATCCAAAACT AAGGTTTATA CTAGACTGCA AATTAATGAA AGGAATTATC   5820

ATTATTGTTT TGTATACTTT CATGACCGAA AACAAGGCTA AACACTATCC ATGTATGAAA   5880

ATTTAAGGCT AAAAGTTGTT CTTAATCATT GCTCCCTTTT GTTTAGGGTT CCCAAATTAT   5940

AGAGGATTCA GTGAAGCCAG TGTCTATCTC GGATGTGGCC ATCACAAGTA CAAACAATCA   6000

TACAGTGGCC CATGGTGAGA TTATAGATGA TCAATCAATG GATGCTGATG AGAAGAAGGT   6060

GGCTAGAAAG AGTCTTACTC GCATTAGGAC AAGTGTTGGT GCTTCGGAGG AATCACAACT   6120

TATTGGGCGA GAGAAAGAAA TATCTGAAAT AACACACTTA ATTTTAAACA ATGATAGCCA   6180

GCAGGTTCAG GTGATCTCTG TGTGGGGAAT GGGTGGCCTT GGAAAAACCA CCCTAGTAAG   6240

CGGTGTTTAT CAAAGCCCAA GGCTGAGTGA TAAGTTTGAC AAGTATGTTT TTGTCACAAT   6300

CATGCGTCCT TCATTCTTTG TAGAGCTCCT TAGGAGTTTG GCTGAGCAAC TACATAAAGG   6360
```

-continued

```
ATCTTCTAAG AAGGAAGAAC TGTTAGAAAA TAGAGTCAGC AGTAAGAAAT CACTAGCATC      6420
GATGGAGGAT ACCGAGTTGA CTGGGCAGTT GAAAAGGCTT TTAGAAAAGA AAAGTTGCTT      6480
GATTGTTCTA GATGATTTCT CAGATACCTC AGAATGGGAC CAGATAAAAC CAACGTTATT      6540
CCCCCTGTTG GAAAAGACAA GCCGAATAAT TGTGACTACA AGAAAAGAGA ATATTGCCAA      6600
CCATTGCTCA GGGAAAAATG GAAATGTGCA CAACCTTAAA GTTCTTAAAC ATAATGATGC      6660
ATTGTGCCTC TTGAGTGAGA AGGTAATATA AGTGTGCTCC ATTTTTCTTG GTTTGATATT      6720
CTTTTAATCA TTTGAGTTAT CCAATCAAGA TGATATTTGT GCATGCAGAA ATAGCATATA      6780
CTAGATTCAT ATACAACTTA ATCTGTTCTC ACAACAATAG CAATGCAGTT CCTAAAATGA      6840
CCTGCATTGG ATGGACGTTA GATGTGACTT TGTTTTTGTA TGTAATGGTG GCCTTCATTC      6900
CTTAGTTTTA ATAGTAAAGA CGTATTTCTA AATTTAATTT TTTTTGTTTT ACTTTAGAGC      6960
ACAATAAAGC TTAAATTGTA TCAATGTCAG GTATTTGAGG AGGCTACATA TTTGATGAT       7020
CAGAACAATC CAGAGTTGGT TAAAGAAGCA AAACAAATCC TAAAGAAGTG CGATGGACTG      7080
CCCCTTGCAA TAGTTGTCAT AGGTGGATTC TTGGCAAACC GACCAAAGAC CCAGAAGAG       7140
TGGAGAAAAT TGAACGAGAA TATCAATGCT GAGTTGGAAA TGAATCCAGA GCTTGGAATG      7200
ATAAGAACCG TCCTTGAAAA AAGCTATGAT GGTTTACCAT ACCATCTCAA GTCATGTTTT      7260
TTATATCTGT CCATTTTCCC TGAAGACCAG ATCATTAGTC GAAGGCGTTT GGTGCATCGT      7320
TGGGCAGCAG AAGGTTACTC AACTGCAGCA CATGGGAAAT CTGCCATTGA AATAGCTAAC      7380
GGCTACTTCA TGGAACTCAA GAATAGAAGC ATGATTTTAC CATTCCAGCA ATCAGGTAGC      7440
AGCAGGAAAT CAATTGACTC TTGCAAAGTC CATGATCTCA TGCGTGACAT CGCCATCTCA      7500
AAGTCAACGG AGGAAAACCT TGTTTTTAGG GTGGAGGAAG GCTGCAGCGC GTACATACAT      7560
GGTGCAATTC GTCATCTTGC TATAAGTAGC AACTGGAAGG GAGATAAGAG TGAATTCGAG      7620
GGCATAGTGG ACCTGTCCCG AATACGATCG TTATCTCTGT TTGGGGATTG GAAGCCATTT      7680
TTTGTTTATG GCAAGATGAG GTTTATACGA GTGCTTGACT TTGAAGGGAC TAGAGGTCTA      7740
GAATATCATC ACCTTGATCA GATTTGGAAG CTTAATCACC TAAAATTCCT TTCTCTACGA      7800
GGATGCTATC GTATTGATCT ACTGCCAGAT TTACTGGGCA ACCTGAGGCA ACTCCAGATG      7860
CTAGACATCA GAGGTACATA TGTAAAGGCT TTGCCAAAAA CCATCATCAA GCTTCAGAAG      7920
CTACAGTACA TTCATGCTGG GCGCAAAACA GACTATGTAT GGGAGGAAAA GCATAGTTTA      7980
ATGCAGAGGT GTCGTAAGGT GGGATGTATA TGTGCAACAT GTTGCCTCCC TCTTCTTTGC      8040
GAAATGTATG GCCCTCTCCA TAAGGCCCTA GCCCGGCGTG ATGCGTGGAC TTTCGCTTGC      8100
TGCGTGAAAT TCCCATCTAT CATGACGGGA GTACATGAAG AGGAAGGCGC TATGGTGCCA      8160
AGTGGGATTA GAAAACTGAA AGACTTGCAC ACACTAAGGA ACATAAATGT CGGAAGGGGA      8220
AATGCCATCC TACGAGATAT CGGAATGCTC ACAGGATTAC ACAAGTTAGG AGTGGCTGGC      8280
ATCAACAAGA AGAATGGACG AGCGTTTCGC TTGGCCATTT CCAACCTCAA CAAGCTGGAA      8340
TCACTGTCTG TGAGTTCAGC AGGGATGCCG GGCTTGTGTG GTTGCTTGGA TGATATATCC      8400
TCGCCTCCGG AAAACCTACA GAGCCTCAAG CTGTACGGCA GTTTGAAAAC GTTGCCGGAA      8460
TGGATCAAGG AGCTCCAGCA TCTCGTGAAG TTAAAACTAG TGAGTACTAG GCTATTGGAG      8520
CACGACGTTG CTATGGAATT CCTTGGGGAA CTACCGAAGG TGGAAATTCT AGTTATTTCA      8580
CCGTTTAAGA GTGAAGAAAT TCATTTCAAG CCTCCGCAGA CTGGGACTGC TTTTGTAAGC      8640
CTCAGGGTGC TCAAGCTTGC AGGATTATGG GGCATCAAAT CAGTGAAGTT TGAGGAAGGA      8700
```

-continued

```
ACAATGCCCA AACTTGAGAG GCTGCAGGTC CAAGGGCGAA TAGAAAATGA AATTGGCTTT      8760

TCTGGGTTAG AGTTTCTCCA AAACATCAAC GAAGTCCAGC TCAGTGTTTG GTTTCCCACG      8820

GATCATGATA GGATAAGAGC CGCGCGCGCC GCGGGCGCTG ATTATGAGAC TGCCTGGGAG      8880

GAAGAGGTAC AGGAAGCAAG GCGCAAGGGA GGTGAACTGA AGAGGAAAAT CCGAGAACAG      8940

CTTGCTCGGA ATCCAAACCA ACCCATCATT ACCTGAGCTC CTTTGGAGTT ACTTTGCCGT      9000

GCTCCATACT ATCCTACAAG TGAGATCCTC TGCAGTACTG CATGCTCACT GACATGTGGA      9060

CCCGAGGGGC TGTGGGGCCC ACATGTCAGT GAGCAGTACT GTGCAGTACT GCAGAGGACC      9120

TGCATCCACT ATCCTATATT ATAATGGATT GTACTATCGA TCCAACTATT CAGATTAACT      9180

CTATACTAGT GAACTTATTT TTTTTTGCCG GGCCGGCAAA TAGCTGGTCG ATGTATATTA      9240

AGAATAAGAA AGGGAATGTA CAAGATAGCG CGGTGCGTCA ATGCACCACC ATTACAGACG      9300

TAAAAGGAAA GCTAAAATCT CACAGAATGA GTTGCTACAG AGTGACACAT GGGGCTAACA      9360

AGACCTGCAG CTATCCAAGT CTCCCATTCA TCCCCCATGG CAGAACAGAA CTGGGGAACC      9420

GTTGCCGCGA TCCCTTCAAA CACCCTTGCG TTTCGCTCTT TCGAAATCAA CCAGGTTACA      9480

AGGATCACCC TTGCATCGAA CGTTTTGCGG TCAACCTTAG CAACAGATTT CCGGGCTGCA      9540

AGCCACCAAT CAGCAAAATC AGCCGACGAT GAGGAGCACG AAAGGACCAG GCGTGTGCGC      9600

ACCTGACCTC AAATCTCCTG GGTGTAAGAG CAGCCCACGA AGATGTGCTG GCAGGTTTCC      9660

CCGTCATTGG AGCAGAAATA GCACACCGGA GCAAGCTTCC ATCTGTGACG TTGTAGATTG      9720

TTGGCAGTGA GGCAAGCATT GCGCTCGGCG AGAAACATAA AGAACTTACA TCTCGCCGGG      9780

GCAAGAGACT TCCAAATAAT GGTATACATA TGTAGTATAT AGTATAGTAT AGTATAGTAT      9840

AAGGGTATTC ATTTTGCAGG TTAGCGGTTA TCTGCTGCTG TTCCTCCTGC TGCGGCGTGC      9900

TGGAGTAGTG TTGTTGGTGG TGGTGCTGAT GACCTAAAAT GCTTGCTTGT TTCTATCAAG      9960

TTCTCCAGAA TGTAGTATGT ACTGCATCTT GTTGATTTTT GTCCATAAAC GGATTGCATT     10020

ATCTGTATAT GACCCAATCA ACAATAAACG GTGTTGCATT TTGTTCCTAA AAGCTCTTAG     10080

AGTCTGACCA GTTATCTCTG TACGCATCTT CATGCTGTTC TTTGGGCACT GGTCATGGTT     10140

AAATCACAGT TCACCGAAAC TTATTTTCTG TAGACTTATT CTGAAATACT GAGAAATTGA     10200

AATGTAGTAA CTATTGTCTG TAGACTGCTT TCTCGTTTTT CTTTTGCGGT CGCCATCTCC     10260

AGTCAGTATC TACAGAAGAA GAGCCAATGC AGCCTATTGT CCTTTTTTTG CCGGGTCGGC     10320

CG                                                                    10322
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:4:

```
AGGGAAAAAT GGAAATGTGC                                                    20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:5:

AGTAACCTTC TGCTGCCCAA                                                   20

(2) INFORMATION FOR SEQ ID NO:6:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid, synthetic DNA (xi) SEQUENCE DESCRIPTION: SEQ ID NO:6:

TTACCATCCC AGCAATCAGC                                                   20

(2) INFORMATION FOR SEQ ID NO:7:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid, synthetic DNA (xi) SEQUENCE DESCRIPTION: SEQ ID NO:7:

AGACACCCTG CCACACAACA                                                   20

(2) INFORMATION FOR SEQ ID NO:8:

(i) SEQUENCE CHARACTERISTICS:
      (A) LENGTH: 52 amino acids
      (B) TYPE: amino acid
      (D) TOPOLOGY: linear (ii) MOLECULE TYPE: protein (xi) SEQUENCE DESCRIPTION: SEQ ID NO:8:

Gly Met Gly Gly Ser Gly Lys Thr Thr Leu Lys Arg Tyr Ile Val Val
 1               5                  10                  15

Leu Asp Asp Val Trp Gly Ser Arg Val Met Met Thr Thr Arg Asp Met
            20                  25                  30

Gln Gly Leu Pro Leu Ala Ile Ala Ser Leu Gly Ser Lys Arg Cys Phe
        35                  40                  45

Leu Tyr Cys Ser
    50

(2) INFORMATION FOR SEQ ID NO:9:

(i) SEQUENCE CHARACTERISTICS:
      (A) LENGTH: 52 amino acids
      (B) TYPE: amino acid
      (D) TOPOLOGY: linear (ii) MOLECULE TYPE: protein (xi) SEQUENCE DESCRIPTION: SEQ ID NO:9:

Gly Pro Gly Gly Val Gly Lys Thr Thr Leu Arg Phe Leu Leu Leu
 1               5                  10                  15

Leu Asp Asp Val Trp Lys Cys Lys Val Met Phe Thr Thr Arg Ser Ile
            20                  25                  30

-continued

```
Gly Gly Leu Pro Leu Ala Leu Ile Thr Leu Gly Gly Arg Ser Cys Phe
        35                  40                  45

Leu Tyr Cys Ala
        50

(2) INFORMATION FOR SEQ ID NO:10:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:10:

Gly Met Gly Gly Val Gly Lys Thr Thr Ile Lys Lys Val Leu Ile Val
 1               5                  10                  15

Leu Asp Asp Ile Asp Gly Ser Arg Ile Ile Ile Thr Thr Arg Asp Lys
                20                  25                  30

Lys Gly Leu Pro Leu Ala Leu Lys Val Trp Gly Ser Ile Ala Cys Phe
        35                  40                  45

Leu Arg Gly Glu
        50

(2) INFORMATION FOR SEQ ID NO:11:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:11:

Gly Met Gly Gly Ile Gly Lys Thr Thr Thr Phe Lys Ile Leu Val Val
 1               5                  10                  15

Leu Asp Asp Val Asp Gln Ser Arg Phe Ile Ile Thr Ser Arg Ser Met
                20                  25                  30

Ala Gly Leu Pro Leu Thr Leu Lys Val Ile Gly Ser Ile Ala Cys Phe
        35                  40                  45

Phe Ile Gly Gln
        50

(2) INFORMATION FOR SEQ ID NO:12:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:12:

Gly Asn Gly Gly Ile Gly Lys Thr Thr Leu Lys Lys Phe Leu Ile Val
 1               5                  10                  15

Leu Asp Asp Val Trp Gly Asn Met Ile Ile Leu Thr Thr Arg Ile Gln
                20                  25                  30

Lys Gly Asn Pro Leu Ala Ala Lys Thr Val Gly Ser Asp Gln Cys Val
        35                  40                  45

Ser Tyr Cys Ser
        50
```

-continued (2) INFORMATION FOR SEQ ID NO:13:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:13:

```
Gly Met Gly Gly Leu Gly Lys Thr Thr Leu Lys Ser Cys Leu Ile Val
 1               5                  10                  15

Leu Asp Asp Phe Ser Thr Ser Arg Ile Ile Val Thr Thr Arg Lys Glu
            20                  25                  30

Asp Gly Leu Pro Leu Ala Ile Val Val Ile Gly Gly Lys Ser Cys Phe
            35                  40                  45

Leu Tyr Leu Ser
        50
```

RICE GENE RESISTANT TO BLAST DISEASE

FIELD OF THE INVENTION

The present invention relates to a gene controlling resistance to blast disease in plants, a protein encoded by said gene, and their use.

BACKGROUND OF THE INVENTION

Blast disease is a serious disease in plants such as rice and is caused by the rice blast fungi, *Magnaporthe grisea*. The disease has substantially damaged the rice yields in Japan and many other rice-breeding countries. The damage is particularly severe at low temperatures and in high humidity. The disease has been obviated by breeding resistant varieties as well as applying agricultural chemicals. Originally, there were rice strains resistant to the disease. These strains and varieties carry genes resistant to a specific race of the blast fungi, and these genes have been analyzed for a long time. Presently, about 30 genes have been identified as being blast-disease resistant (Kinoshita, Rice Genet. Newsl. 7:16–57 (1990), Iwata, Rice Genet. Newsl. 13:12–35 (1996), Iwata, Rice Genet. Newsl. 14:7–22 (1997)). These genes have been utilized to breed highly resistant varieties, and in consequence, a number of resistant varieties have been bred. However, the introduced resistance genes are becoming ineffective due to the emergence of novel races of the blast fungi (collapse of resistant varieties). Furthermore, the molecular mechanisms of expression of the blast disease resistance and the interaction between the rice blast fungi and resistance genes remain unknown.

The resistance gene Pi-b is located at the end of the long arm of rice chromosome 2 and displays resistance to all races of blast fungi identified in Japan except for 033b (Table 1).

TABLE 1

| | | Fungal strain | | | | | | | | |
|---|---|---|---|---|---|---|---|---|---|---|
| Variety | Gene | Ine #003 | Cho #007 | 2101 #013 | Ine #031 | THB9 #033 b+ | Cho #035 | F67- #047 | Ine #101 | P-2b #303 | Ai74 - #477 |
| Shin 2 | — | S | S | S | S | S | S | S | S | S | S |
| Aichiasahi | Pi-a | S | S | S | R | S | R | S | R | S | S |
| Inabawase | Pi-i | R | S | R | R | R | S | S | R | R | S |
| Kanto 51 | Pi-k | R | R | S | S | S | S | R | R | R | S |
| Tsuyuake | Pi-km | R | R | R | S | S | S | R | R | R | S |
| Fukunishiki | Pi-z | R | R | R | R | R | S | R | R | S |
| Yashiromochi | Pi-ta | R | R | R | R | R | R | R | R | S | R |
| Pi No.4 | Pi-ta2 | R | R | R | R | R | R | R | R | S | R |
| Toride 1 | Pi-zt | R | R | R | R | R | R | R | R | R | S |
| Ouu 316 | Pi-b | R | R | R | R | S | R | R | R | R | R |

R: resistant
S: susceptible

The gene has been carried in Indica varieties such as Engkatek, Milek Kuning, Tjina, and Tjahaja in Indonesia and Malaysia. In Japan, TohokuIL9, a strain homozygous for the Pi-b and having a genetic background of the sensitive variety Sasanishiki, has been bred at the Miyagi Prefectural Furukawa Agriculture Experimental Station. However, the mechanism of the resistance expression has not been clarified, nor has the Pi-b gene been isolated.

SUMMARY OF THE INVENTION

An objective of the present invention is to provide Pi-b, a resistance gene to the blast disease, a functionally equivalent gene, and proteins encoded by the genes. Another objective is to create a plant resistant to the blast disease by utilizing the gene.

The present inventors have succeeded in isolating the rice blast disease resistance gene by using map-based cloning to isolate the gene Pi-b from a large chromosomal region. Specifically, the inventors performed linkage analysis using molecular markers. First, the Pi-b locus was assigned to a chromosomal region between specific markers. Next, a physical map was constructed by aligning cosmid clones near the assigned region. The nucleotide sequences of the clones were then determined to find the region of the Pi-b candidate gene containing the nucleotide binding site (NBS) that is commonly found in the resistance genes of several plants. A cDNA library was then constructed from a variety resistant to the blast disease. The library was screened using the above candidate genomic region as a probe, and a cDNA corresponding to said genomic region was isolated. Using oligonucleotide primers prepared based on the nucleotide sequence of the isolated cDNA, RT-PCR was performed on each MRNA fraction prepared from varieties sensitive and resistant to the blast disease to analyze the expression pattern of the isolated Pi-b candidate cDNA. The cDNA was specifically amplified in the resistant variety. The present inventors thus found that the isolated cDNA clone is the Pi-b gene. The present inventors also found that plants resistant to the blast disease can be created by utilizing the isolated gene or genes homologous thereto because there is a close relationship between the isolated gene and the resistance to the blast disease.

The present invention relates to the rice blast disease resistance gene Pi-b, homologous genes, and proteins encoded by the genes. The invention also relates to a method of producing a plant resistant to the blast disease by using the genes. More specifically, the present invention relates to the following:

(1) A protein that confers on plants resistance to the blast disease, wherein the protein comprises the amino acid sequence of SEQ ID NO: 1, or its modified sequence in which one or more amino acids are substituted, deleted, and/or added, (2) A protein that confers on plants resistance to the blast disease, wherein the protein is encoded by a DNA that hybridizes with a DNA comprising the nucleotide sequence of SEQ ID NO: 2 and/or No: 3, (3) A DNA encoding the protein of (1) or (2), (4) A vector comprising the DNA of (3), (5) A host cell carrying the vector of (4), (6) The host cell of (5), wherein said host cell is a plant cell, (7) A method of producing the protein of (1) or (2), wherein the method comprises cultivating the host cell of (5), (8) A transformed plant comprising the host cell of (6), (9) The plant of (8), wherein said plant is the Poaceae,

(10) The plant of (8), wherein said plant is *P. oryza*, (11) The plant of any one of (8), (9), or (10), wherein said plant displays resistance to the blast disease,

(12) An antibody that binds to the protein of (1) or (2), and

(13) A DNA comprising at least 15 nucleotides, wherein the DNA hybridizes specifically to the DNA of (3).

BRIEF DESCRIPTION OF THE DRAWINGS

FIG. 4 compares the Pi-b gene and the conserved regions of known resistance genes.

DETAILED DESCRIPTION OF THE INVENTION

Figure 1:
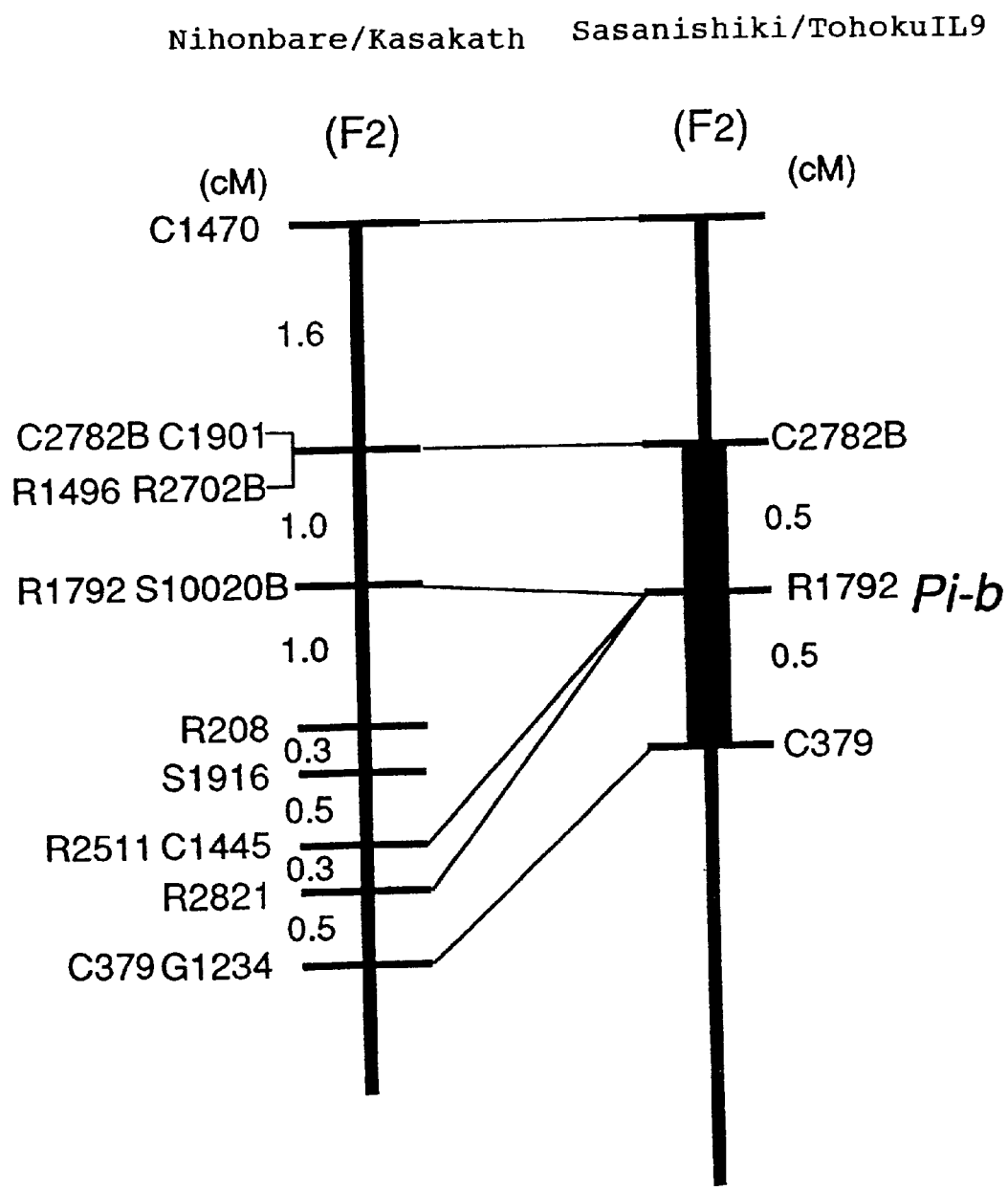
FIG. 1 schematically shows the presumed region of the Pi-b locus by crude-scale linkage analysis.

The present invention relates to a protein that confers on plants a phenotype resistant to the blast disease. The amino acid sequence of a protein encoded by the "Pi-b" gene (hereinafter called the Pi-b protein), which is included in a protein of the present invention, is shown in SEQ ID NO: 1. The Pi-b gene, which encodes a protein that confers on rice a phenotype resistant to the blast disease, was known to be located somewhere within a large region of rice chromosome 2. The present inventors are the first to succeed in identifying its locus and isolating the gene as a single gene. The Pi-b protein confers resistance to all races of the rice blast fungi in Japan except 033b on rice. This is the broadest range of resistance among the genes identified so far (Table 1). These characteristics of the Pi-b protein suggest that the Pi-b protein or a protein functionally equivalent thereto is quite suitable for creating plant varieties resistant to the blast disease.

It is possible to produce a protein functionally equivalent to the Pi-b protein by, for example, the method described below. A method of introducing mutations into the amino acid sequence of the Pi-b protein is well known to one skilled in the art. Namely, one skilled in the art can alter the amino acid sequence of the Pi-b protein (SEQ ID NO: 1) by site-directed mutagenesis (Kramer, W. and Fritz, H. -J. Oligonucleotide-directed construction of mutagenesis via gapped duplex DNA, Methods in Enzymology 154:350–367, (1987)) to produce a mutant protein, which is functionally equivalent to the Pi-b protein. Mutations of amino acids can occur spontaneously. The protein of the present invention includes a protein having an amino acid sequence of the wild type Pi-b protein with one or more amino acids being substituted, deleted, or added, and functionally equivalent to the wild type Pi-b protein. The site and number of altered amino acid residues in a protein is not limited as long as the altered protein is functionally equivalent to the wild type Pi-b protein. There are usually not more than 50 altered amino acid residues, preferably not more than 30, more preferably not more than 10, and most preferably not more than 3. For example, proteins functionally equivalent to the Pi-b protein can be produced by conservative amino acid substitutions at one or more amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The phrase "functionally equivalent to the wild type Pi-b protein" used herein means that the altered protein confers resistance to the blast disease on plants. The phrase "to confer resistance to the blast disease on plants" means that the protein confers resistance to at least one race of the rice blast fungi on at least one plant variety. The plant on which resistance is to be conferred is preferably the Poaceae, and more preferably *Poaceae oryza*. Whether a protein confers resistance to the blast disease on plants can be judged by, for example, (i) inoculating the rice blast fungi on juvenile plants (from three to four-week-old seedlings of rice, for example) by directly spraying with a suspension of spores formed by a certain race of the rice blast fungi, (ii) incubating the inoculated plant at 25° C. in 100% humidity for 24 hours immediately after inoculation, then cultivating under normal conditions for about two weeks, (iii) observing whether local lesions will stop outgrowth due to specific necrosis as a result of hypersensitive reaction (a plant carrying a resistance gene), or the local lesions will continue to outgrow causing plant death (a plant without a resistance gene).

Also, the hybridization technique (Southern, E. M., J. Mol. Biol. 98, 503 (1975)) and the polymerase chain reaction (PCR) technique (Saiki, R. K. et al., Science 230:1350–1354, (1985); Saiki, R. K. et al., Science 239:487–491, (1988)) are known to one skilled in the art as other methods to produce a functionally equivalent protein. Namely, one skilled in the art can usually isolate a DNA that is highly homologous to the Pi-b gene from rice or other plants, using the nucleotide sequence of the Pi-b gene (SEQ ID NO: 2 or No: 3) or its portion as a probe, or using oligonucleotide primers that hybridize specifically to the Pi-b gene (SEQ ID NO: 2 or No: 3), to obtain a protein functionally equivalent to the Pi-b protein from said DNA. The protein of the present invention includes a protein functionally equivalent to the Pi-b protein that is isolated by the hybridization technique or the PCR technique. The phrase "functionally equivalent to the Pi-b protein" used herein means that the protein isolated by the hybridization technique or the PCR technique confers resistance to the blast disease on plants. The plants to be used for isolating a gene by the above technique include, besides rice, crops that are possible hosts of the blast fungi, such as Hordeum, Triticum, Setaria, Panicum, Echinochloa, and Coix (Crop Disease Encyclopedia, (1988), Kishi, K. ed. Japan Agriculture Education Association). Normally, a protein encoded by the isolated gene has a high homology to the Pi-b protein at the amino acid level when the protein is functionally equivalent to the Pi-b protein. The high homology means preferably a homology of 30% or more, more preferably of 50% or more, still more preferably of 70% or more, and most favorably of 90% or more.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions) ×100). In one embodiment the two sequences are the same length.

To determine percent homology between two sequences, the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877 is used. Such an algorithm is incorporated into the NBLAST and XBLAST programs of Altschul, et al. (1990) *J. Mol. Biol.* 215:403–410. BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to a Pi-b protein molecules. To obtain gapped alignments for comparison purposes, Gapped BLAST is utilized as described in Altschul et al. (1997) *Nucleic Acids Res.* 25:3389–3402. When utilizing BLAST and Gapped BLAST programs, the default parameters of the respective programs (e.g., XBLAST and NBLAST) are used. See http://www.ncbi.nlm.nih.gov.

The protein of the present invention can be produced as a recombinant protein using methods known to one skilled in the art by means of the recombinant DNA technology, or as a natural protein. For example, a recombinant protein can be produced by inserting a DNA encoding the protein of the present invention into an appropriate expression vector, introducing said vector into appropriate cells, and then purifying the protein from said transformed cells. A natural protein can be prepared by, for example, exposing the extracts of cells (rice cells, for example) expressing the protein of the present invention to an affinity column packed with an antibody prepared by immunizing an appropriate immune animal with a recombinant protein or its portion, and purifying bound proteins from said column.

The present invention also relates to a DNA encoding the protein of the present invention. The DNA of the present invention is not limited and includes a genomic DNA, a cDNA, and a chemically synthesized DNA as long as the DNA encodes a protein of the present invention. The nucleotide sequences of the Pi-b cDNA and the Pi-b genomic DNA of the present invention are shown in SEQ ID NO: 2 and NO: 3, respectively.

One skilled in the art can prepare a genomic DNA or a cDNA using the standard methods. For example, a genomic DNA can be prepared in two steps. First, construct a genomic library (utilizing a vector such as plasmid, phage, cosmid, or BAC) using genomic DNA extracted from leaves of a rice variety (TohokuIL9, for example) carrying a resistance gene to the blast disease. Second, perform colony hybridization or plaque hybridization on the spread library using a probe prepared based on the nucleotide sequence of a DNA encoding a protein of the present invention (SEQ ID NO: 1 or NO: 2, for example). Alternatively, a genomic DNA can be prepared by performing PCR using specific primers to a DNA encoding a protein of the present invention (SEQ ID NO: 1 or NO: 2, for example). A cDNA can also be prepared by, for example, synthesizing cDNA from MRNA extracted from leaves of a rice variety (TohokuIL9, for example) carrying a resistance gene to the blast disease, inserting the CDNA into a vector such as XZAP to construct a cDNA library, and performing colony hybridization or plaque hybridization on the spread library, or by performing PCR as described above.

A DNA of the present invention can be utilized for preparing a recombinant protein or creating transformed plants resistant to the blast disease. A recombinant protein is usually prepared by inserting a DNA encoding a protein of the present invention into an appropriate expression vector, introducing said vector into an appropriate cell, culturing the transformed cells, and purifying expressed proteins. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or as being tagged with histidine (Novagen, pET series). The host cell is not limited as long as the cell is suitable for expressing the recombinant protein. It is possible to utilize yeasts or various animal, plant, or insect cells besides the above described *E. coli*. A vector can be introduced into host cells by various methods known to one skilled in the art. For example, a transformation method using calcium ions (Mandel, M. and Higa, A., J. Mol. Biol. 53:158–162, (1970); Hanahan, D., J. Mol. Biol. 166:557–580, (1983)) can be used to introduce a vector into *E. coli*. A recombinant protein expressed in host cells can be purified by known methods. When a recombinant protein is expressed as a fusion protein with maltose binding protein or other partners, the recombinant protein can be easily purified by affinity chromatography.

A transformed plant resistant to the blast disease can be created using a DNA of the present invention. Namely, a DNA encoding a protein of the present invention is inserted into an appropriate vector, the vector is introduced into a plant cell, and the resulting transformed plant cell is regenerated. The vector is not limited as long as the vector can express inserted genes in plant cells. For example, vectors containing a promoter for constitutive gene expression in plant cells (such as cauliflower mosaic virus 35S promoter, for example), or a promoter inducible by exogenous stimuli can be used. The plant cell to be transfected with the vector is not limited, but Poaceae cells are favorable. Besides rice, examples of the cells include Hordeum, Triticum, Setaria, Panicum, Echinochloa, and Coix. The term "plant cell" used herein includes various forms of plant cells, such as a cultured cell suspension, a protoplast, a leaf section, and a callus. A vector can be introduced into plant cells by a known method such as the polyethylene glycol method, electroporation, Agrobacterium mediated transfer, and particle bombardment. Plants can be regenerated from transformed plant cells depending on the type of the plant cell by a known method (Toki et al., (1995) Plant Physiol. 100:1503–1507).

Furthermore, the present invention relates to an antibody that binds to a protein of the present invention. The antibody of the present invention can be either a polyclonal antibody or a monoclonal antibody. A polyclonal antibody can be prepared by immunizing immune animals such as rabbits with a purified protein of the present invention or its portion, collecting blood after a certain period, and removing clots. A monoclonal antibody can be prepared by fusing myeloma cells and the antibody-forming cells of animals immunized with the above protein or its portion, isolating a monoclonal cell expressing a desired antibody (hybridoma), and recovering the antibody from the said cell. The obtained antibody can be utilized for purifying or detecting a protein of the present invention.

Furthermore, the present invention relates to a DNA that specifically hybridizes to a DNA encoding a protein of the present invention and comprises at least 15 nucleotide residues. The phrase "specifically hybridizes" used herein means that the DNA hybridizes with a DNA encoding a protein of the present invention but not with any DNA encoding other proteins in standard hybridization conditions. The DNA can be used, for example, as a probe to detect or isolate a DNA encoding a protein of the present invention, or as a primer for PCR amplification. An example is DNA consisting of at least 15 nucleotides complementary to the nucleotide sequence of SEQ ID NO: 2 or NO: 3.

Standard hybridization conditions (e.g., moderate or highly stringent conditions) are known to those skilled in the art and can be found in *Current Protocols in Molecular Biology*, John Wiley & Sons, N.Y. (1989), 6.3.1–6.3.6, hereby incorporated by reference. Moderate hybridization conditions are defined as equivalent to hybridization in 2× sodium chloride/sodium citrate (SSC) at 30° C., followed by one or more washes in 1× SSC, 0.1% SDS at 50–60° C. Highly stringent conditions are defined as equivalent to hybridization in 6× sodium chloride/sodium citrate (SSC) at 45° C., followed by one or more washes in 0.2× SSC, 0.1% SDS at 50–65° C.

The present invention provides the blast disease resistance gene Pi-b, functionally equivalent genes thereof, and proteins encoded by the genes. The disease resistance gene of the present invention can confer a resistance to a broad range of the rice blast fungi on plants. Therefore, the gene will greatly contribute to controlling the disease and increasing crop yields, for example, when introduced into beneficial crops such as rice.

The present invention is illustrated in detail below with reference to examples but is not to be construed as being limited thereto.

EXAMPLE 1

Crude-scale linkage analysis

To identify the approximate region of the Pi-b gene on the linkage map of rice chromosome 2, linkage analysis using DNA markers was first performed. The source used was a segregating population of 94 plants, resulting from self-fertilization of the F1 progeny derived from two back crosses between Sasanishiki and the F1 progeny from a cross between Sasanishiki and TohokuIL9. This linkage analysis revealed that the Pi-b gene was located between RFLP markers C2782 and C379 in chromosome 2 and cosegregated with R1792, R257, and R2821 (Japanese Society of Breeding, the 87th meeting, FIG. 1).

EXAMPLE 2

Fine-scale linkage analysis

A large segregating population was analyzed to isolate the gene. From the above population of 94 plants, 20 plants that are heterozygous for the Pi-b locus were selected, and a segregating population of about 20,000 seeds, including self-fertilized seeds, was used for the analysis (Japanese Society of Breeding, the 89th meeting). In the analysis, the pool sampling method was applied to minimize the task (Churchill et al., *Proc. Natl. Acad. Sci. USA* 90:16–20 (1993)).

Figure 2:
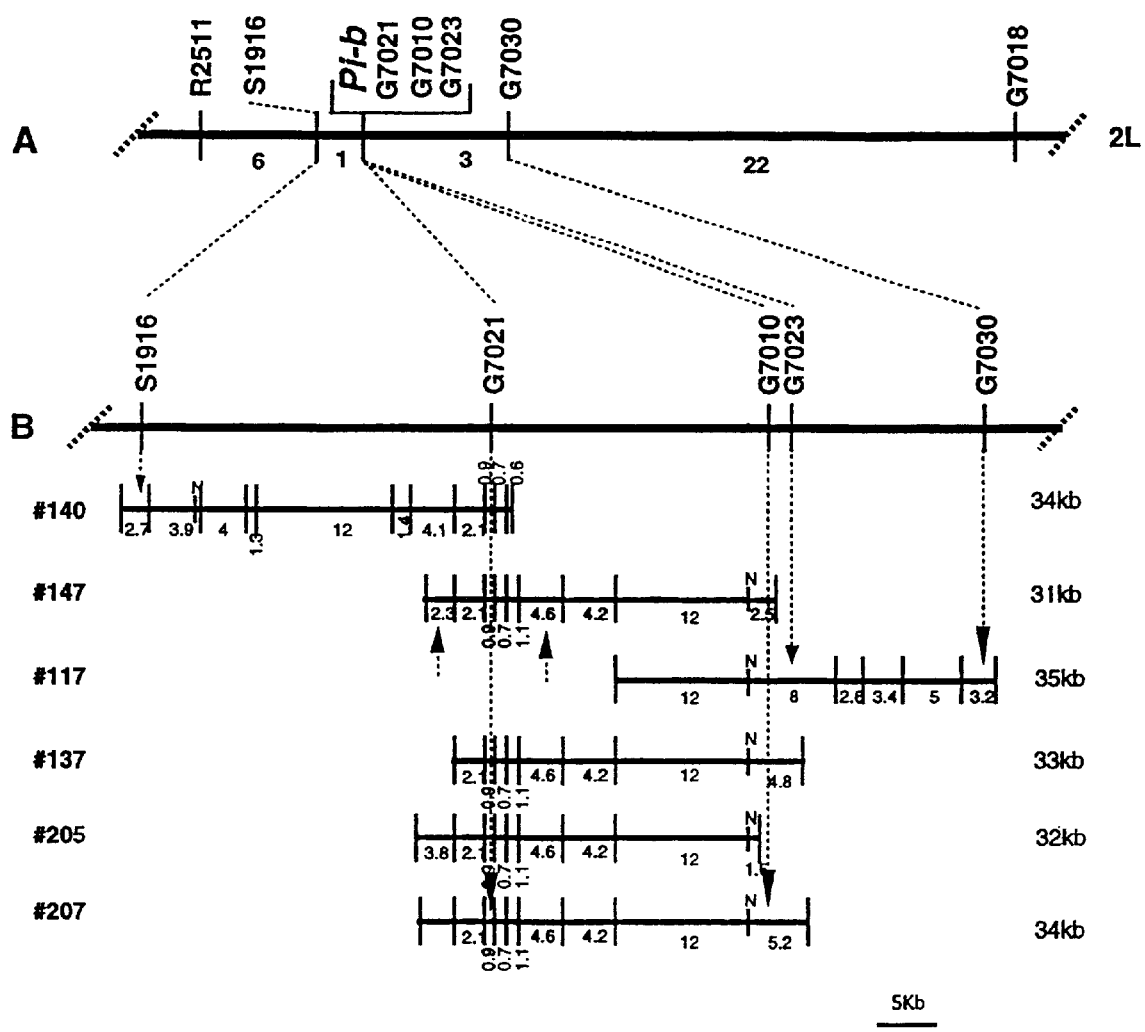
FIGS. 2A–2B schematically show the presumed region of the Pi-b locus by fine-scale linkage analysis.

To increase the accuracy of linkage analysis, it is necessary to increase the number of DNA markers near the target gene and to enlarge the sampling population. Accordingly, YAC clones carrying the Pi-b locus, which was determined by the crude-linkage analysis, were subcloned to increase the number of DNA markers near the Pi-b gene (Monna et al., *Theor. Appl. Genet.* 94:170–176 (1997)). This linkage analysis using a large population narrowed the Pi-b locus down to a region between RFLP markers S1916 and G7030. In addition, the Pi-b gene was co-segregated with three RFLP markers (G7010, G7021, and G7023; FIG. 2).

EXAMPLE 3

Alignment of the Pi-b locus using cosmid clones

To further narrow down the Pi-b locus, cosmid clones were used for alignment. Genomic DNA was extracted from TohokuIL9 carrying the resistance gene by the CTAB method. The DNA was then partially digested with restriction endonuclease Sau3A. From the digestion product, fragments of about 30 to 50 kb were fractionated by sucrose density gradient centrifugation. The resulting DNA fragments and the cosmid vector SuperCos (Stratagene, Wahl et al., *Proc. Natl. Acad. Sci. USA* 84:2160–2164 (1987)) were used to construct a cosmid library. The cosmid library was screened using five DNA clones near the Pi-b locus (S1916, G7010, G7021, G7023, and G7030) as probes. As a result, six cosmid clones (COS140, COS147, COS117, COS137, COS205, and COS207) were selected. Construction of the restriction maps of these clones and examination of their overlapping regions revealed that the Pi-b locus is in the genome region covered by three clones (COS140, COS147, and COS117; FIG. 2).

EXAMPLE 4

Determination of the candidate genomic region by sequence analysis

Three aligned cosmid clones, which are presumed to contain the Pi-b gene, were subcloned, and their nucleotide sequences were partially analyzed. The obtained nucleotide sequences were analyzed by BLAST homology search on the public nucleotide database. As a result, partial nucleotide sequences of a 2.3 kb clone obtained from COS140, and of a 4.6 kb clone from COS147 were revealed to contain a nucleotide binding site (NBS) that is commonly found in the resistance genes of several plants, such as the RPM1 disease resistance gene in Arabidopsis. Therefore, these nucleotide sequences were expected to be candidate regions for the Pi-b gene.

EXAMPLE 5

Isolation of cDNA and sequence analysis

The cDNA was isolated to examine whether the candidate regions revealed by the nucleotide sequence analysis are expressed in resistant variety TohokuIL9. The resistant variety TohokuIL9 was seeded, and the seedlings of the 4-leaf stage were inoculated with the rice blast fungi TH68-141 (race 003) according to the standard method. The leaves were then collected at three time points, 6 hours, 12 hours, and 24 hours after inoculation. Messenger RNA was extracted from the samples and a cDNA library was constructed. A 1 kb fragment (from positions 3471 to 4507 in SEQ ID NO: 3), obtained by further subcloning the 2.3 kb fragment of the candidate genomic region, was used as a probe to screen the library. As a result, eight cDNA clones were selected. Sequence analysis of the clones revealed that the nucleotide sequence of c23 completely matches that of the cosmid clone COS140. Thus, the candidate genomic region was confirmed to be expressed in TohokuIL9. The selected c23 clone is approximately 4 kb and is assumed to contain almost the entire region of the gene. The complete nucleotide sequence of this clone was determined (SEQ ID NO: 2).

EXAMPLE 6

Analysis of the candidate cDNA expression pattern

Figure 3:
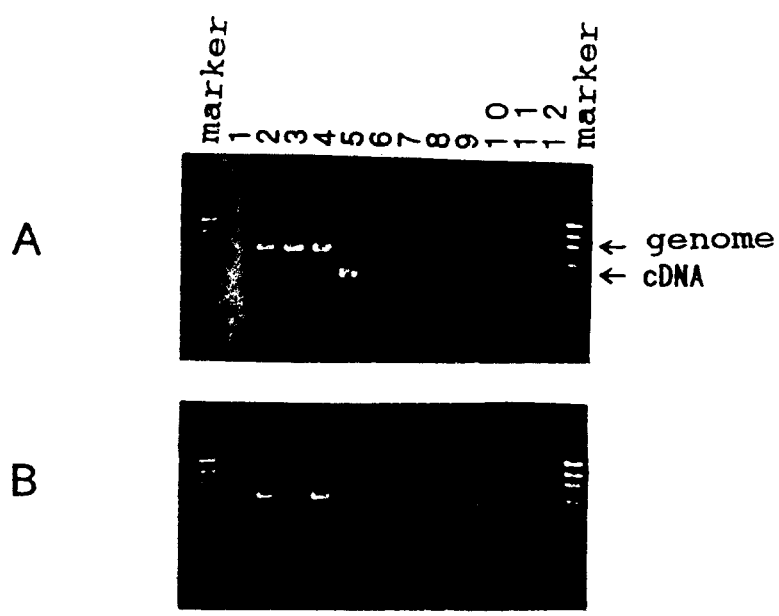
FIGS. 3A–3B show a photograph of electrophoretic patterns indicating the result of RT-PCR analysis for the expression of the Pi-b candidate cDNA in varieties sensitive and resistant to the blast disease. In A, primers encompassing the second intron of the cDNA clone c23 were used. In B, primers specific to the 4.6 kb fragment, which contains the NBS adjacent to the region c23, were used. The template used was composed of genomic DNAs from Sasanishiki and TohokuIL9 in lanes 1 and 2; cosmid clones #40 and #147 originating from TohokuIL9 in lanes 3 and 4, respectively; plasmid DNA containing the cDNA c23 from TohokuIL9 in lane 5; mRNA (2000 ng; the same amount shall apply for mRNA hereinafter) prepared from untreated leaves of TohokuIL9 in lane 6; MRNA prepared from leaves of TohokuIL9 12 hours, 24 hours, or 4 days after inoculation with the rice blast fungi in lanes 7, 8, and 9, respectively; MRNA from untreated leaves of Sasanishiki in lane 10; MRNA prepared from leaves of Sasanishiki 12 and 24 hours after inoculation with the fungi in lanes 10 and 11, respectively; and sterilized water in lane 12. The size markers are 1.4 K, 1.0 K, 0.9 K, and 0.6 K from the top.

Differences in expression patterns of the candidate cDNA region were revealed in a sensitive variety (Sasanishiki) and a resistant variety (TohokuIL9). The above two varieties were inoculated with the race 003 of the rice blast fungi at the 4-leaf stage , and leaves were collected at 6 hours, 12 hours and 24 hours after inoculation. MRNA was then extracted and used as a template for RT-PCR. Primers SEQ ID NO: 4/5'-AGGGAAAAATGGAAATGTGC-3' (antisense) and SEQ ID NO: 5/5'-AGTAACCTTCTGCTGCCCAA-3' (sense)) based on the nucleotide sequence of the cDNA clone c23 were designed for RT-PCR to specifically amplify the region. PCR was performed with a cycle of 94° C. for 2 minutes; 30 cycles of 94° C. for 1 minute, 55° C. for 2 minutes, and 72° C. for 3 minutes; and a cycle of 72° C. for 7 minutes. After PCR, a specific amplification was detected in a resistant variety of TohokuIL9, but no amplification was detected using MRNA from a sensitive variety (Sasanishiki; FIG. 3). This suggests that CDNA clone c23 is specifically expressed in resistant varieties. Also, RT-PCR was performed using primers SEQ ID NO: 6/5'-TTACCATCCCAGCAATCAGC-3' (sense) and SEQ ID NO: 7/5'-AGACACCCTGCCACACAACA-3' (antisense), based on the nucleotide sequence of the 4.6 kb fragment which contains the NBS and is adjacent to the c23 region. The region of the 4.6 kb fragment was not amplified in either a sensitive variety (Sasanishiki) or a resistant variety (TohokuIL9; FIG. 3). It is strongly suggested that the genomic region corresponding to clone c23 is the Pi-b locus.

EXAMPLE 7

Sequence analysis of the genomic DNA of the Pi-b candidate gene

The complete nucleotide sequence of the genomic region corresponding to cDNA clone c23 was determined. The cosmid clone COS140 was subcloned by cleaving with five different restriction enzymes, and the nucleotide sequences of the resulting subclones were determined from both ends as much as possible. The regions that were not accessible by the above analysis were cut shorter by deletion, and subjected to DNA sequencing. The determined region extends to 10.3 kb (SEQ ID NO: 3).

EXAMPLE 8

Structure of the Pi-b gene

The Pi-b candidate cDNA c23 is 3925 base pairs in full-length and has an ORF of 3618 base pairs containing three exons separated by two introns. The Pi-b translated product is a protein of 1205 amino acid residues (SEQ ID NO: 1), having two NBSs (P-loop at amino acid positions 386–395 and Kinase 2 at positions 474–484) and three conserved regions (domain 1 at amino acid positions 503–513, domain 2 at positions 572–583, and domain 3 at positions 631–638) which are found in many resistance genes. These domains show a high homology to the conserved regions of known resistance genes such as RPM1 (FIG. 4)(SEQ ID NO: 8). Also, the gene has 12 incomplete, leucine-rich repeats (LRR at amino acid positions 755–1058) in the 3' side. These structures show an extremely high homology to the resistance genes of the NBS-LRR class previously reported. Based on the above results, the present inventors concluded that the analyzed CDNA and the corresponding genomic region are the rice blast disease resistance gene Pi-b.

---

What is claimed is:

1. An isolated DNA encoding a protein that confers on a plant resistance to a blast disease caused by a fungal pathogen, wherein the protein comprises the amino acid sequence of SEQ ID NO: 1.

2. A vector comprising the isolated DNA of claim 1.

3. A host cell comprising the vector of claim 2.

4. A method of producing a transformed plant, comprising: introducing the vector of claim 2 into a plant cell to produce a transformed plant cell, and allowing the transformed plant cell to regenerate a plant.

5. The host cell of claim 3, wherein said host cell is a plant cell.

6. A method of producing a protein, wherein the method comprises cultivating the host cell of claim 3 under conditions in which the protein is produced.

7. A method of producing a protein, comprising: cultivating the host cell of claim 3 under conditions in which the protein is produced; and purifying the protein from said host cell.

8. A transformed *Oryza saliva* comprising the host cell of claim 5, wherein said *Oryza saliva* displays resistance to blast disease caused by *Magnaporthe grisea*.

9. The isolated DNA of claim 1, wherein the plant is *Oryza saliva* and the fungal pathogen is *Magnaporthe grisea*.

10. An isolated DNA encoding a protein that confers on a plant resistance to blast disease caused by a fungal pathogen, said DNA comprising a nucleotide sequence which hybridizes under highly stringent conditions to the nucleotide sequence of SEQ ID NO: 2 or SEQ ID NO: 3.

11. The isolated DNA of claim 10, wherein the plant is *Oryza saliva* and the fungal pathogen is *Magnaporthe grisea*.

12. An isolated DNA encoding a protein that confers on a plant resistance to blast disease caused by a fungal pathogen, said protein having an amino acid sequence which is 90% identical to the amino acid sequence of SEQ ID NO: 1.

13. The isolated DNA of claim 12, wherein the plant is *Oryza saliva* and the fungal pathogen is *Magnaporthe grisea*.

14. An isolated DNA comprising the nucleotide sequence of SEQ ID NO: 2.

15. An isolated DNA comprising the nucleotide sequence of SEQ ID NO: 3.

16. An isolated DNA encoding a protein which comprises the amino acid sequence of SEQ ID NO: 1.

\* \* \* \* \*

UNITED STATES PATENT AND TRADEMARK OFFICE
CERTIFICATE OF CORRECTION

PATENT NO. : 6,274,789 B1
DATED : August 14, 2001
INVENTOR(S) : Masahiro Yano et al.

It is certified that error appears in the above-identified patent and that said Letters Patent is hereby corrected as shown below:

Column 3,
Lines 35, 38 and 39, delete "MRNA" and insert -- mRNA --.

Column 6,
Line 25, delete "MRNA" and insert -- mRNA --.
Line 27, delete "CDNA" and insert -- cDNA --.
Line 27, delete "XZAP" and insert -- λZAP --.

Column 9,
Line 41, delete "MRNA" and insert -- mRNA --.

Column 10,
Line 2, delete "MRNA" and insert -- mRNA --.
Lines 4 and 48, delete "CDNA" and insert -- cDNA --.

Column 39,
Lines 43, 44 and 47, delete "*saliva*" and insert -- *sativa* --.

Column 40,
Lines 30 and 39, delete "*saliva*" and insert -- *sativa* --.

Signed and Sealed this

Twenty-second Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,274,789 B1
DATED         : August 14, 2001
INVENTOR(S)  : Masahiro Yano et al.

It is certified that error appears in the above-identified patent and that said Letters Patent is hereby corrected as shown below:

Title page,
Item [73], Assignee, add Assignee -- National Institute of Agrobiological Sciences (JP) --

Signed and Sealed this

Twelfth Day of October, 2004

JON W. DUDAS
*Director of the United States Patent and Trademark Office*